(12) United States Patent
Garza et al.

(10) Patent No.: US 12,427,234 B2
(45) Date of Patent: Sep. 30, 2025

(54) MEDICAL FLUID CASSETTE LEAK DETECTION METHODS AND DEVICES

(71) Applicant: Fresenius Medical Care Holdings, Inc., Waltham, MA (US)

(72) Inventors: Hernando Garrido Garza, Brentwood, CA (US); Akbar Doctor, Concord, CA (US); Preetam Kodam, Dublin, CA (US); Dante Marchetti, Danville, CA (US); John Jacob, Mountain House, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 1241 days.

(21) Appl. No.: 17/195,825

(22) Filed: Mar. 9, 2021

(65) Prior Publication Data

US 2022/0288290 A1  Sep. 15, 2022

(51) Int. Cl.
*A61M 1/14* (2006.01)
*A61M 1/00* (2006.01)

(52) U.S. Cl.
CPC .......... *A61M 1/155* (2022.05); *A61M 1/1522* (2022.05); *A61M 1/1524* (2022.05); *A61M 1/154* (2022.05); *A61M 1/159* (2022.05); *A61M 1/802* (2021.05); *A61M 2205/15* (2013.01); *A61M 2205/18* (2013.01);
(Continued)

(58) Field of Classification Search
CPC .... A61M 1/155; A61M 1/802; A61M 1/1524; A61M 1/522; A61M 1/159; A61M 1/54; A61M 2205/15; A61M 2205/18; A61M 2205/3334; A61M 2205/50; A61M 2205/581; A61M 2205/582; A61M 2205/583; A61M 1/14; A61M 1/154; A61M 1/1615; A61M 1/1647
See application file for complete search history.

(56) References Cited

U.S. PATENT DOCUMENTS 9,593,678 B2   3/2017 Gray et al.
2005/0126998 A1  6/2005 Childers
(Continued)

OTHER PUBLICATIONS

Cosmo-k.co.jp [online], "The Advantages of Using Air Leak Testers," retrieved on Jul. 13, 2020, retrieved from URL <https://www.cosmo-k.co.jp/english/leak-test/leak-technology/leak-merit/>, 3 pages.
(Continued)

*Primary Examiner* — Lauren P Farrar
(74) *Attorney, Agent, or Firm* — Fish & Richardson P.C.

(57) ABSTRACT

This disclosure relates to medical fluid cassette leak detection methods and devices. In some implementations, a method of detecting micro-leaks in a medical fluid cassette, the method includes decreasing a pressure between a vacuum reservoir of a medical treatment machine and a membrane of the medical fluid cassette when the medical fluid cassette is coupled to the medical treatment machine; measuring, using a flow meter, a rate of net fluid flow between the vacuum reservoir and the membrane of the medical fluid cassette; determining that the rate of net fluid flow between the vacuum reservoir and the membrane of the medical fluid cassette is above a threshold value; and in response to determining that the rate of net fluid flow is above the threshold value, causing the medical treatment machine to take a particular action.

29 Claims, 10 Drawing Sheets

(52) U.S. Cl.
CPC . *A61M 2205/3334* (2013.01); *A61M 2205/50* (2013.01); *A61M 2205/581* (2013.01); *A61M 2205/582* (2013.01); *A61M 2205/583* (2013.01)

(56) References Cited

U.S. PATENT DOCUMENTS

| | | | |
|---|---|---|---|
| 2007/0016152 A1 | 1/2007 | Karpowicz et al. | |
| 2011/0077605 A1* | 3/2011 | Karpowicz | A61M 1/86 604/319 |
| 2014/0034557 A1 | 2/2014 | Günther et al. | |
| 2014/0276421 A1* | 9/2014 | Plahey | A61M 1/16 73/40.5 R |
| 2017/0286638 A1* | 10/2017 | Searle | G16H 40/63 |
| 2018/0207343 A1 | 7/2018 | Spickermann et al. | |
| 2020/0038778 A1 | 2/2020 | Schwan et al. | |
| 2020/0191682 A1 | 6/2020 | Plahey et al. | |

OTHER PUBLICATIONS

Honeywell, "Honeywell Zephyr Digital Airflow Sensors: HAF Series-High Accuracy 50 SCCM to 750 SCCM," Jun. 2015, retrieved from URL <http://www.mouser.com/datasheet/2/187/honeywell-sensing-airflow-zephyr-haf-series-digita-740409.pdf>, 15 pages.

Pfeiffer Vacuum [online], "Leak detection methods—part 7: Micro-Flow (overpressure test)," May 25, 2018, retrieved on May 10, 2021, <https://www.youtube.com/watch?v=k_YdNIGuWD8>, 3 pages [Video Submission].

Extended European Search Report in European Appln. No. 22767653.3, dated Jun. 26, 2024, 8 pages.

International Preliminary Report on Patentability in International Appln. No. PCT/US2022/017438, mailed Sep. 21, 2023, 7 pages.

International Search Report and Written Opinion in International Appln. No. PCT/US2022/017438, mailed Jun. 7, 2022, 13 pages.

* cited by examiner

MEDICAL FLUID CASSETTE LEAK DETECTION METHODS AND DEVICES

TECHNICAL FIELD

This disclosure relates to medical fluid cassette leak detection methods and devices.

BACKGROUND

Dialysis is a treatment used to support a patient with insufficient renal function. The two principal dialysis methods are hemodialysis and peritoneal dialysis.

During hemodialysis ("HD"), the patient's blood is passed through a dialyzer of a dialysis machine while also passing dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), a patient's peritoneal cavity is periodically infused with dialysate. The membranous lining of the patient's peritoneum acts as a natural semi-permeable membrane that allows diffusion and osmosis exchanges to take place between the solution and the blood stream. These exchanges across the patient's peritoneum, like the continuous exchange across the dialyzer in HD, result in the removal of waste products, including solutes like urea and creatinine, from the blood, and regulate the levels of other substances, such as sodium and water, in the blood.

Many PD machines are designed to automatically infuse, dwell, and drain dialysate to and from the patient's peritoneal cavity. The treatment typically lasts for several hours, often beginning with an initial drain cycle to empty the peritoneal cavity of used or spent dialysate. The sequence then proceeds through the succession of fill, dwell, and drain phases that follow one after the other. Each phase is called a cycle.

SUMMARY

In one aspect, a method of detecting micro-leaks in a medical fluid cassette, the method includes decreasing a pressure between a vacuum reservoir of a medical treatment machine and a membrane of the medical fluid cassette when the medical fluid cassette is coupled to the medical treatment machine; measuring, using a flow meter, a rate of net fluid flow between the vacuum reservoir and the membrane of the medical fluid cassette; determining that the rate of net fluid flow between the vacuum reservoir and the membrane of the medical fluid cassette is above a threshold value; and in response to determining that the rate of net fluid flow is above the threshold value, causing the medical treatment machine to take a particular action.

Implementations can include one or more of the following features in any combination.

In some implementations, causing the medical treatment machine to take a particular action includes causing the medical treatment machine to generate at least one of an audible indication, a visual indication, and a tactile indication.

In certain implementations, the at least one of an audible indication, a visual indication, and a tactile indication indicates to a user that the membrane of the medical fluid cassette has a micro-leak.

In some implementations, the at least one of an audible indication, a visual indication, and a tactile indication includes a message displayed on a screen of the medical treatment machine.

In certain implementations, wherein the at least one of an audible indication, a visual indication, and a tactile indication includes an audible warning emitted by a speaker of the medical treatment machine.

In some implementations, causing the medical treatment machine to take a particular action includes terminating a treatment being carried out by the medical treatment machine.

In certain implementations, causing the medical treatment machine to take a particular action includes disabling the medical treatment machine until the medical fluid cassette is replaced with a new medical fluid cassette that does not contain a leak.

In some implementations, the flow meter includes a micro-flow meter; and measuring the rate of net fluid flow between the membrane of the medical fluid cassette and the vacuum reservoir of the medical treatment machine includes monitoring, using the micro-flow meter, the rate of net fluid flow between the membrane and the vacuum reservoir of the medical treatment machine during application of a vacuum pressure on membrane of the medical fluid cassette during a testing period.

In certain implementations, the medical treatment machine is a dialysis machine; and the medical fluid cassette is a dialysis fluid cassette.

In some implementations, the medical treatment machine is configured to perform a peritoneal dialysis treatment.

In certain implementations, the medical fluid cassette is a medical fluid pumping cassette.

In some implementations, the medical fluid pumping cassette is a dialysate pumping cassette.

In certain implementations, the threshold value is between 1.25 cc/min and 1.75 cc/min.

In some implementations, the method further includes determining that the rate of net fluid flow is above the threshold value indicates that the membrane of the medical fluid cassette has an opening through the membrane no greater than 0.005 inches in diameter In certain implementations, the method further includes determining that the rate of net fluid flow is above an upper boundary; and in response to determining that the rate of net fluid flow is above an upper boundary, identifying the medical fluid cassette as having a leak greater than a micro-leak.

In a further aspect, a medical treatment system includes a medical fluid cassette including a body and a membrane affixed to the body; a medical fluid treatment machine including a vacuum reservoir; a flow meter positioned between the vacuum reservoir and the membrane of the medical fluid cassette when the medical fluid cassette is coupled to the medical fluid treatment machine; and at least one processor. The at least one processor is configured to perform operations including controlling the medical fluid treatment machine to decrease a pressure between the vacuum reservoir and the membrane of the medical fluid cassette; receiving, from the flow meter, data indicating a rate of net fluid flow between the vacuum reservoir and the membrane of the medical fluid cassette; determining, based on the data received from the flow meter, that the rate of net fluid flow between the vacuum reservoir and the membrane of the medical fluid cassette is above a threshold value; and in response to determining that the rate of net fluid flow is above the threshold value, causing the medical fluid treatment machine to take a particular action.

Implementations can include one or more of the following features in any combination.

In certain implementations, wherein causing the medical fluid treatment machine to take a particular action includes causing the medical fluid treatment machine to generate at least one of an audible indication, a visual indication, and a tactile indication. In some implementations, the at least one of an audible indication, a visual indication, and a tactile indication indicates to a user that the membrane of the medical fluid cassette has a micro-leak.

In certain implementations, the at least one of an audible indication, a visual indication, and a tactile indication includes a message displayed on a screen of the medical fluid treatment machine.

In some implementations, the at least one of an audible indication, a visual indication, and a tactile indication includes an audible warning emitted by a speaker of the medical fluid treatment machine.

In certain implementations, causing the medical fluid treatment machine to take a particular action includes terminating a treatment being carried out by the medical fluid treatment machine.

In some implementations, causing the medical fluid treatment machine to take a particular action includes disabling the medical fluid treatment machine until the medical fluid cassette is replaced with a new medical fluid cassette that does not contain a leak.

In certain implementations, the medical fluid treatment machine is a dialysis machine.

In some implementations, the medical fluid treatment machine includes a vacuum line fluidly coupling the vacuum reservoir and the membrane of the medical fluid cassette; and the flow meter includes a micro-flow meter positioned along the vacuum line.

In certain implementations, the data indicating the rate of net fluid flow between the vacuum reservoir and the membrane of the medical fluid cassette includes fluid flow measurements captured by the flow meter during a particular testing period.

In some implementations, the medical treatment machine is configured to perform a peritoneal dialysis treatment.

In certain implementations, the medical fluid cassette is a medical fluid pumping cassette.

In some implementations, the medical fluid pumping cassette is a dialysate pumping cassette.

In certain implementations, the threshold value is between 1.25 cc/min and 1.75 cc/min.

In some implementations, detecting that the rate of net fluid flow is above the threshold value indicates that the membrane of the medical fluid cassette has an opening through the membrane no greater than 0.005 inches in diameter.

In certain implementations, wherein the medical fluid treatment machine includes a surface that abuts the medical fluid cassette when the medical fluid cassette is coupled to the medical fluid treatment machine, and the surface defines one or more vacuum ports.

In some implementations, the medical fluid treatment machine includes a base; and a door connected to the base, the door and the base cooperating to form a cassette compartment configured to receive the medical fluid cassette.

In certain implementations, the medical fluid treatment machine includes a piston configured to be aligned with a pumping chamber defined by the medical fluid cassette when the medical fluid cassette is coupled to the medical fluid treatment machine.

In some implementations, the medical fluid treatment machine includes a pump fluidly coupled to the vacuum reservoir; and controlling the medical fluid treatment machine to decrease a pressure between the vacuum reservoir and the membrane of the medical fluid cassette includes operating the pump.

In a further aspect, a method of testing a medical fluid cassette includes increasing a pressure within a medical fluid cassette using a pressure reservoir fluidly coupled to the medical fluid cassette; measuring, using a flow meter, a rate of net fluid flow between the pressure reservoir and the medical fluid cassette during a testing period; determining that the rate of net fluid flow between the pressure reservoir and the medical fluid cassette is above a threshold value; and in response to determining that the rate of net fluid flow is above the threshold value, identifying the medical fluid cassette as having a micro-leak.

Implementations can include one or more of the following features in any combination.

In certain implementations, the threshold value is between 1.25 cc/min and 1.75 cc/min.

In some implementations, identifying the medical fluid cassette as having a micro-leak indicates that a membrane of the medical fluid cassette has an opening through the membrane no greater than 0.005 inches in diameter.

In certain implementations, an air line fluidly couples the pressure reservoir and the medical fluid cassette; and the flow meter comprises a micro-flow meter that is positioned along the air line.

In some implementations, the method further includes, in response to identifying the medical fluid cassette as having a micro-leak, discarding the medical fluid cassette.

In certain implementations, identifying the medical fluid cassette as having a micro-leak includes marking the medical fluid cassette as defective.

In some implementations, the method further includes, prior to coupling pressurizing the cassette, covering the cassette with a protective cover.

In certain implementations, the protective cover comprises a porous material having a stiffness greater than the stiffness of a membrane of the medical fluid cassette.

In some implementations, increasing the pressure within a medical fluid cassette comprises closing inlets and outlets of the cassette.

In certain implementations, the method further includes, in response to determining that the rate of net fluid flow is above the threshold value: releasing pressure from the medical fluid cassette; increasing the medical fluid cassette a second time using the pressure reservoir fluidly coupled to the medical fluid cassette; measuring, using the flow meter, a second rate of net fluid flow between the pressure reservoir the medical fluid cassette during a second testing period; determining that the second rate of net fluid flow between the pressure reservoir and the medical fluid cassette during the second testing period is above the threshold value; and in response to determining that the second rate of net fluid flow during the second testing period is above the threshold value, discarding the medical fluid cassette.

In some implementations, the testing period ranges from about 8 seconds to about 12 seconds after increasing pressure in the cassette.

In some implementations, a method of determining whether a medical fluid cassette (e.g., a PD fluid cassette) is leaking includes measuring a rate of net flow between the cassette and a vacuum source or a pressure source using a micro-flow meter following application of a pressure (negative or positive, respectively) to the cassette. Based on detecting that the rate of net flow between the cassette and the vacuum source or pressure source is above a threshold amount of flow, the cassette is identified as having a micro-leak. This method is advantageous over some conventional leak detection methods since it is capable of detecting leaks that are below the detection threshold of standard pressure decay tests. In addition, this method is advantageous over some conventional leak detection methods because this method is not dependent on the volume of fluid provided to the cassette during leak testing. In addition, this method is more accurate and precise than many standard leak tests, such as standard pressure decay tests, due to the high level of accuracy of the micro-flow sensors used to perform the methods described herein. In addition, implementations described herein can reduce the likelihood for fluid leaks occurring during treatment by testing a medical fluid cassette using air prior to initiating treatment using the medical fluid cassette.

In some implementations, the dialysis machine, upon detecting a micro-leak, can alert the user to take remedial action such as replacing the cassette with a different cassette before the micro-leak develops into a larger leak and permanent damage to the dialysis machine or to certain critical components of the dialysis machine occurs. In addition, by detecting a micro-leak in a cassette prior to treatment, the risk of interrupted dialysis treatments due to development of a leak during treatment can be mitigated.

In some implementations, a micro-leak can be detected in a cassette as part of manufacturing or post-manufacturing testing, and, upon detecting that the cassette has a micro-leak, the cassette can be preemptively discarded before it is provided to the patient. As a result, potential damage to the dialysis machine or to certain critical components of the dialysis machine can be avoided.

The details of one or more embodiments are set forth in the accompanying drawings and the description below. Other features, objects, and advantages of the disclosure will be apparent from the description and drawings, and from the claims.

DETAILED DESCRIPTION

In general, this disclosure relates to methods of detecting leaks in medical fluid cassettes, and medical fluid pumping machines equipped to perform the methods.

Figure 1:
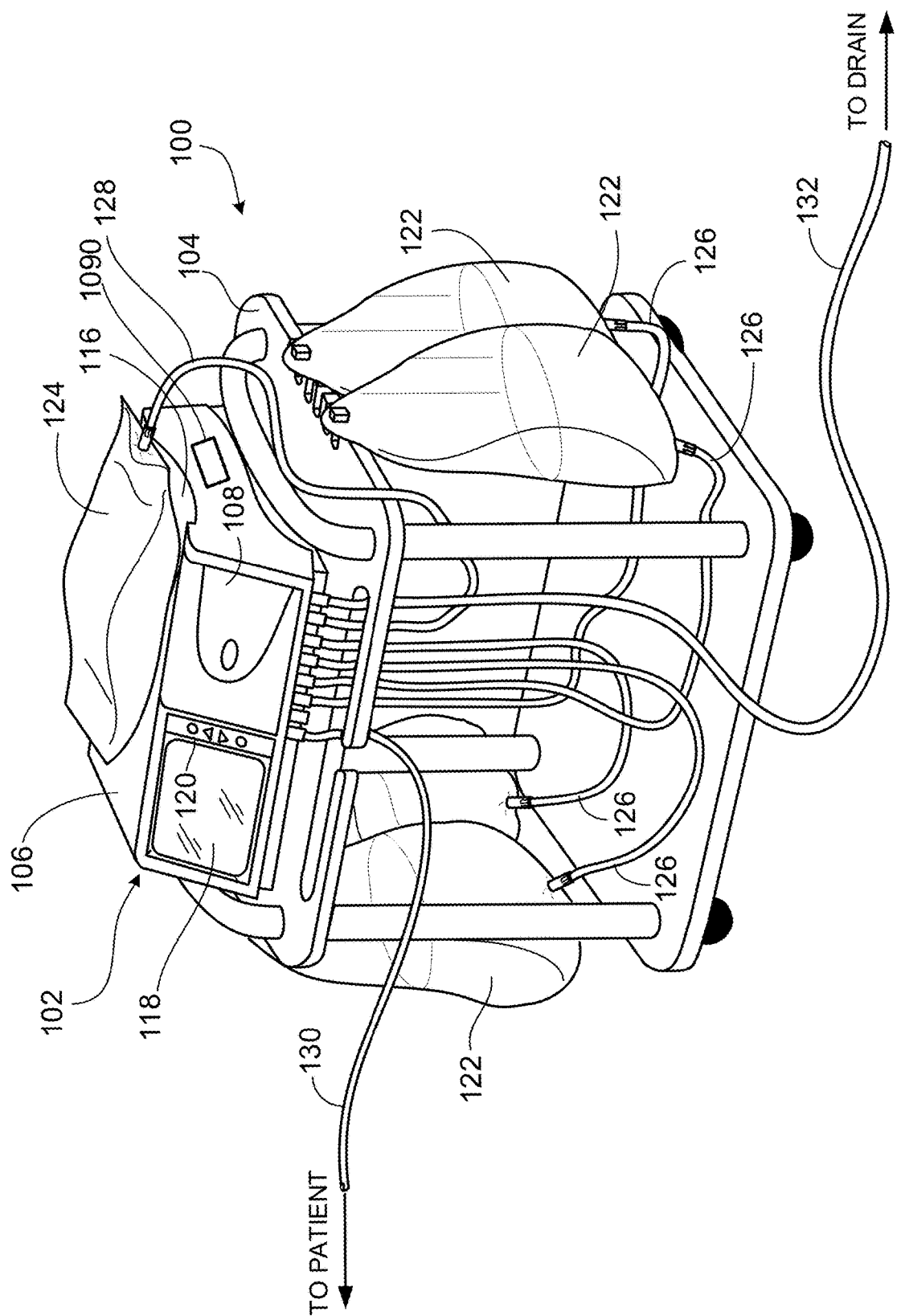
FIG. 1 is a perspective view of a peritoneal dialysis ("PD") system that includes a PD cycler positioned atop a portable cart.
Figure 2:
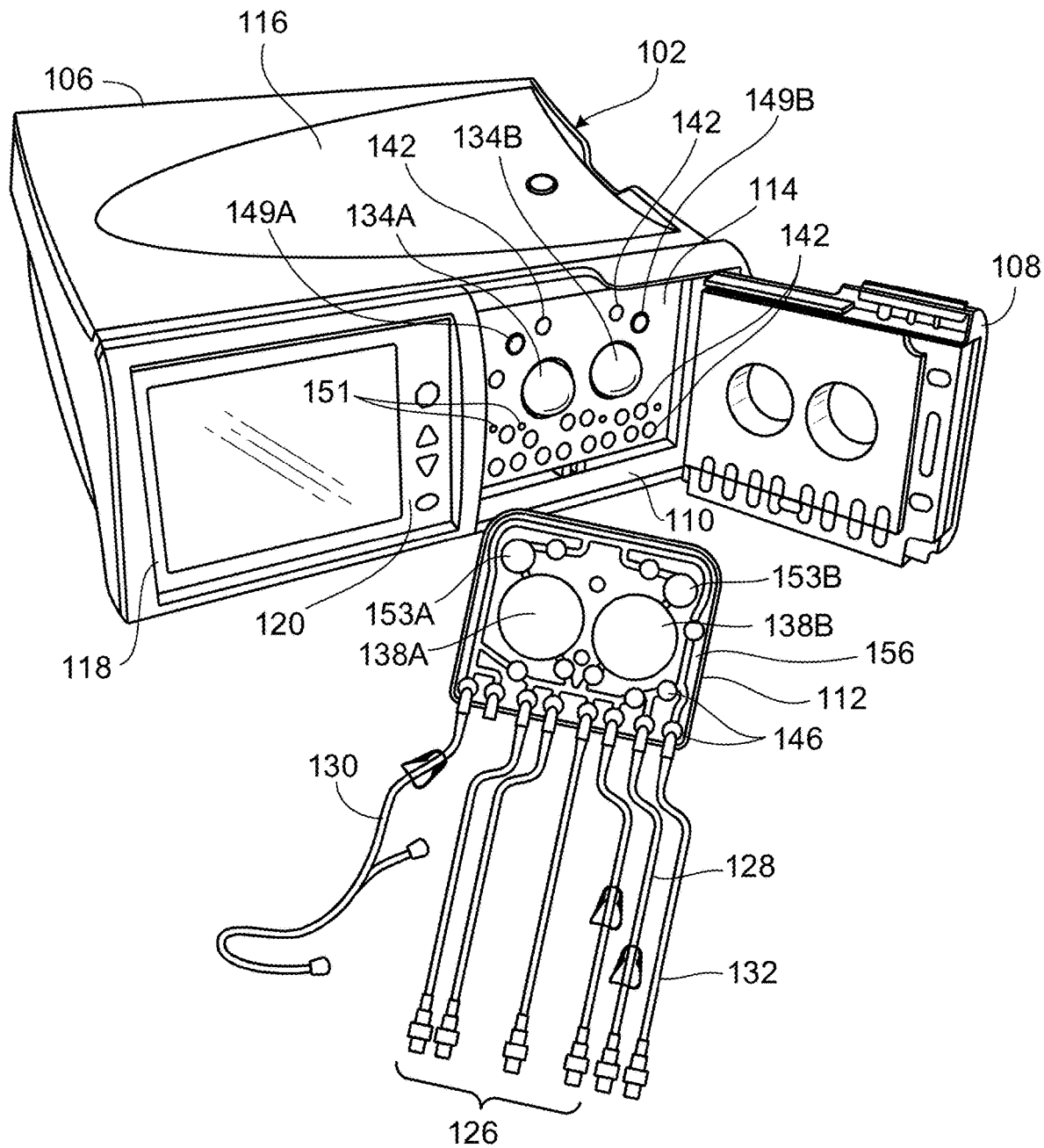
FIG. 2 is a perspective view of the PD cycler and a PD cassette of the PD system of FIG. 1, with a door of the PD cycler in the open position to show the inner surfaces of the PD cycler that interfaces with the PD cassette during use.

Referring to FIGS. 1 and 2, a peritoneal dialysis ("PD") system 100 includes a PD cycler (also referred to as a PD machine) 102, and a disposable PD fluid cassette 112 disposed within the PD cycler 102. The PD cycler 102 is seated on a cart 104. The PD cycler 102 includes a housing 106, a door 108, and a cassette interface 110 that mates with the cassette 112 when the cassette 112 is disposed within a cassette compartment 114 formed between the cassette interface 110 and the door 108. As discussed below, the cassette 112 includes a flexible membrane 140 secured to a rigid base 156 to form pump chambers 138A, 138B and fluid passages through which dialysate passes during use. A heater tray 116 is positioned on top of the housing 106. The heater tray 116 is sized and shaped to accommodate a bag of dialysate (e.g., a 5 liter bag of dialysate). The PD cycler 102 also includes a touch screen 118 and additional control buttons 120 that can be operated by a user (e.g., a patient) to allow, for example, set-up, initiation, and/or termination of a PD treatment.

Dialysate bags 122 are suspended from fingers on the sides of the cart 104, and a heater bag 124 is positioned on the heater tray 116. The dialysate bags 122 and the heater bag 124 are connected to the cassette 112 via dialysate bag lines 126 and a heater bag line 128, respectively. The dialysate bag lines 126 can be used to pass dialysate from the dialysate bags 122 to the cassette 112 during use, and the heater bag line 128 can be used to pass dialysate back and forth between the cassette 112 and the heater bag 124 during use. In addition, a patient line 130 and a drain line 132 are connected to the cassette 112. The patient line 130 can be connected to a patient's abdomen via a catheter and can be used to pass dialysate back and forth between the cassette 112 and the patient during use. The drain line 132 can be connected to a drain or drain receptacle and can be used to pass dialysate from the cassette 112 to the drain or drain receptacle during use.

Figure 3:
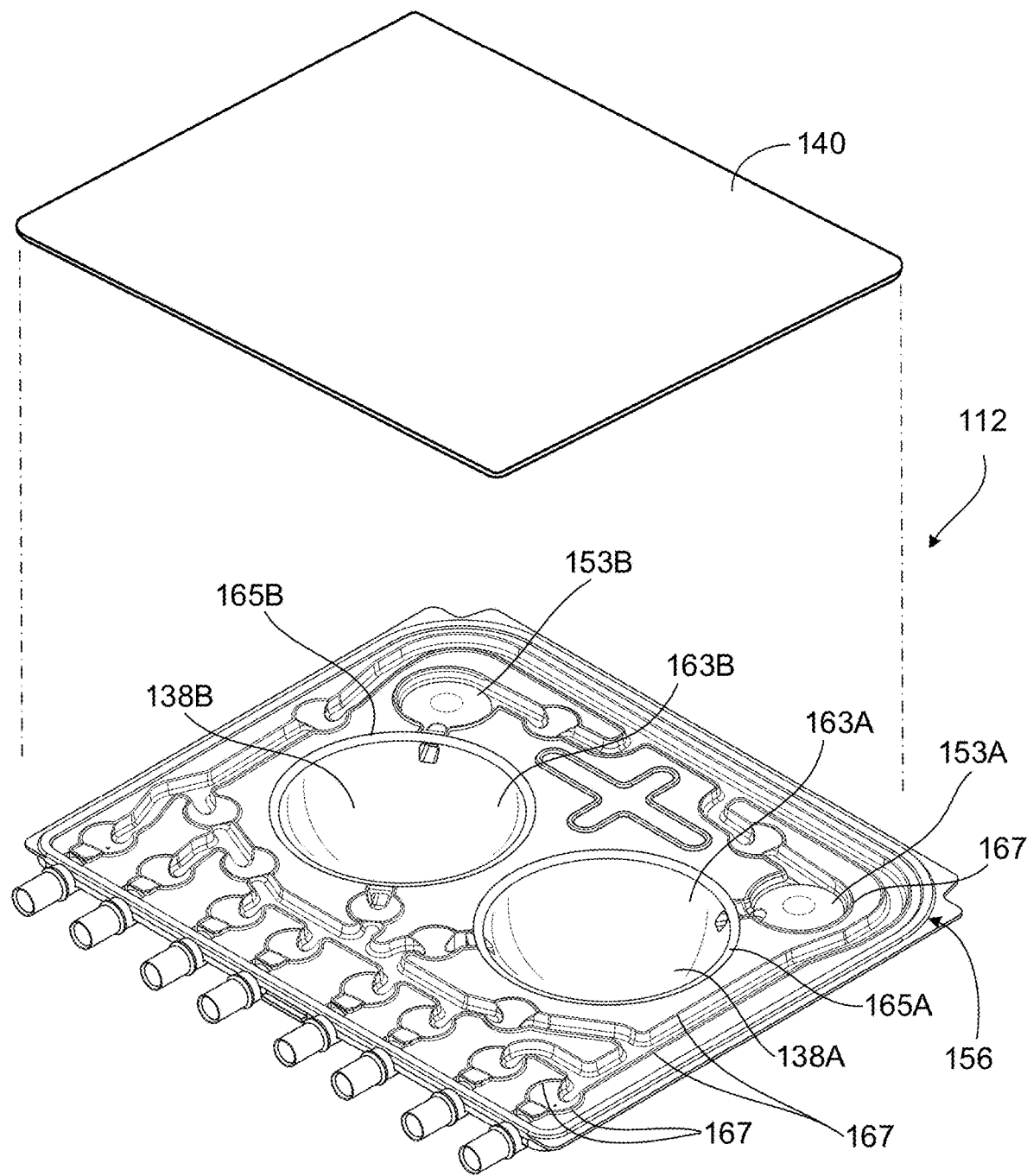
FIG. 3 is an exploded, perspective view of the PD cassette of the PD system of FIG. 1.

First the cassette 112 will be described. That discussion will be followed by a description of the PD cycler 102. FIG. 3 is an exploded, perspective view of the cassette 112. As shown in FIG. 3, the cassette 112 includes the tray-like rigid base 156 and a flexible membrane 140, which is attached to the periphery of the base 156 when the cassette 112 is fully assembled. The base 156 includes recessed regions 163A, 163B that partially define the pump chambers 138A, 138B of the cassette 112. Raised ridges 165A, 165B extend from a planar surface of the base 156 around each of the recessed regions 163A, 163B and extend towards and into contact with the inner surface of the flexible membrane 140 when the cassette 112 is compressed between the door 108 and the cassette interface 110 of the PD cycler 102. In addition to the raised ridges 165A, 165B surrounding the recessed regions 163A, 163B, a series of raised ridges 167 extend from the planar surface of the base 156 towards and into contact with the inner surface of the flexible membrane 140 when the cassette 112 is compressed between the door 108 and the cassette interface 110 of the PD cycler 102.

Figure 4:
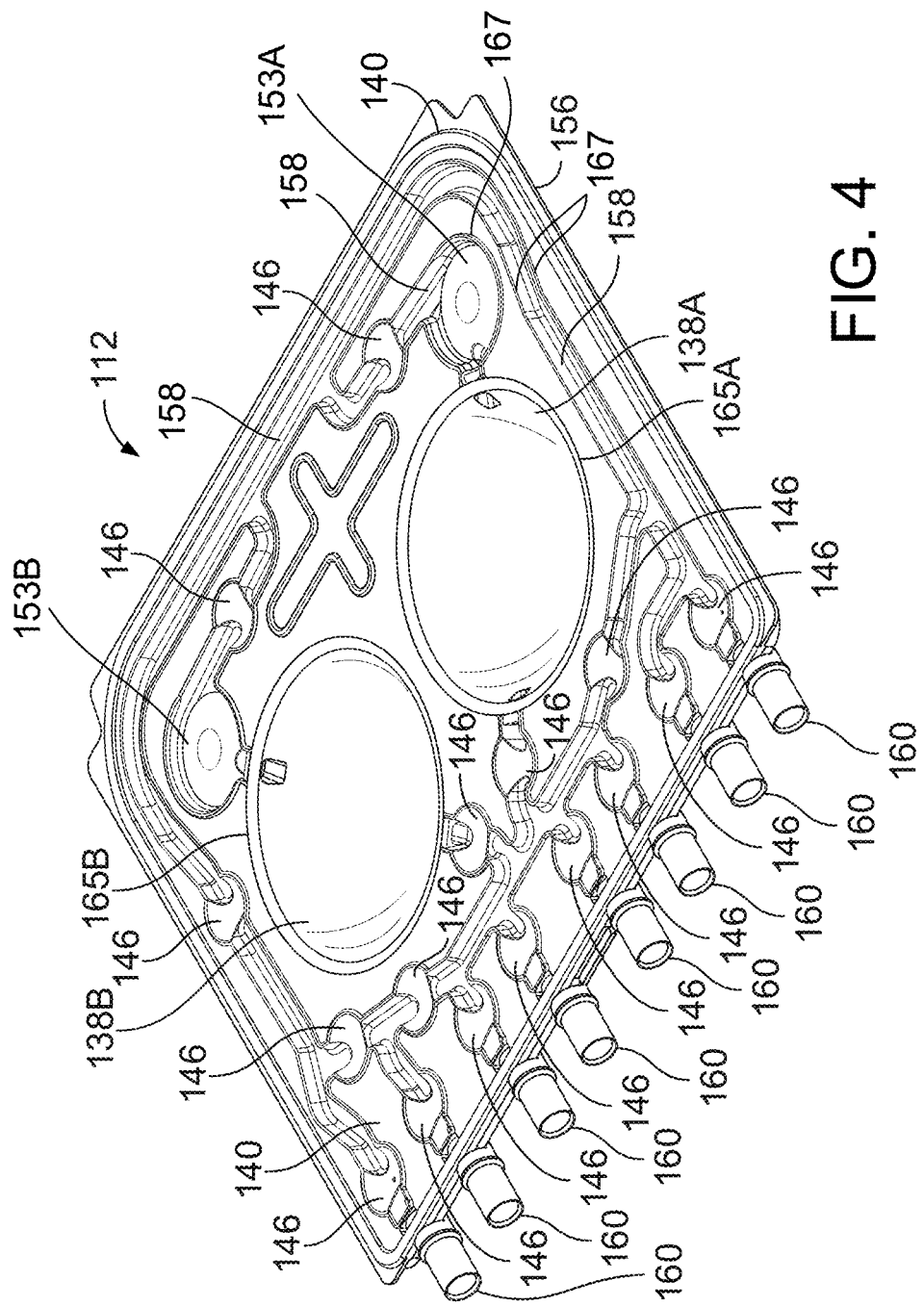
FIG. 4 is a perspective view of the assembled PD cassette of FIG. 3. A rigid base of the cassette is visible through a clear flexible membrane that is attached to the base.

FIG. 4 is a perspective view of the assembled cassette 112. The features of the rigid base 156 are visible through the transparent flexible membrane 140. Referring to both FIGS. 3 and 4, the recessed regions 163A, 163B of the base 156 cooperate with the flexible membrane 140 to form the pump chambers 138A, 138B when the cassette 112 is compressed between the door 108 and the cassette interface 110 of the PD cycler 102 resulting in the flexible membrane 140 being pressed against the raised ridges 165A, 165B of the base 156. In particular, the volumes between the membrane 140 and the hollow projections that form the recessed regions 163A, 163B of the base 156 serve as the pump chambers 138A, 138B. The membrane 140, when compressed against the base 156, similarly cooperates with the series of raised ridges 167 extending from the base 156 to form a series of fluid pathways 158 and to form multiple, depressible dome regions 146, which are widened portions (e.g., substantially circular widened portions) of the fluid pathways 158. The membrane 140, when compressed against the base 156, also cooperates with certain raised ridges 167 to form pressure sensor chambers 153A, 153B.

During treatment, liquid, such as dialysate, flows to and from the pump chambers 138A, 138B through the fluid pathways 158 and the dome regions 146. At each depressible dome region 146, the membrane 140 can be deflected to contact the planar surface of the base 156 from which the raised ridges 167 extend. Such contact can substantially impede (e.g., prevent) the flow of dialysate along the region of the pathway 158 associated with that dome region 146. Thus, as described in further detail below, the flow of dialysate through the cassette 112 can be controlled through the selective depression of the depressible dome regions 146 by selectively inflating mating inflatable members on the cassette interface 110 of the PD cycler 102.

As noted above, the membrane 140 is attached (e.g., adhesively and/or thermally bonded) to the periphery of the base 156. The portion of the membrane 140 overlying the central portion of the base 156 is not necessarily attached to the base 156. Rather, this portion of the membrane 140 may sit loosely atop the raised ridges 165A, 165B, 167 extending from the planar surface of the base 156. The thickness and material(s) of the membrane 140 are selected so that the membrane 140 has sufficient flexibility to flex toward the base 156 in response to the force applied to the membrane 140 by piston heads and inflatable members of the PD cycler 102, which will be described in greater detail below. In certain implementations, the membrane 140 is about 0.100 micron to about 0.150 micron in thickness. However, various other thicknesses may be sufficient depending on the type of material used to form the membrane 140.

Any of various different medical grade materials that permit the membrane 140 to deflect in response to movement of the piston heads and inflation of the inflatable members of the PD cycler 102 without tearing can be used to form the membrane 140. In some implementations, the membrane 140 includes a three-layer laminate. In certain implementations, for example, inner and outer layers of the laminate are formed of a compound that is made up of 60 percent Septon® 8004 thermoplastic rubber (i.e., hydrogenated styrenic block copolymer) and 40 percent ethylene, and a middle layer is formed of a compound that is made up of 25 percent Tuftec® H1062 (SEBS: hydrogenated styrenic thermoplastic elastomer), 40 percent Engage® 8003 polyolefin elastomer (ethylene octene copolymer), and 35 percent Septon® 8004 thermoplastic rubber (i.e., hydrogenated styrenic block copolymer). The membrane 140 can alternatively include more or fewer layers and/or can be formed of different materials.

As shown in FIG. 4, fluid line connectors 160 are positioned along the bottom edge of the cassette 112. The fluid pathways 158 in the cassette 112 lead from the pumping chambers 138A, 138B to the various connectors 160. The connectors 160 are configured to receive fittings on the ends of the dialysate bag lines 126, the heater bag line 128, the patient line 130, and the drain line 132. One end of the fitting can be inserted into and bonded to its respective line and the other end can be inserted into and bonded to its associated connector 160. By permitting the dialysate bag lines 126, the heater bag line 128, the patient line 130, and the drain line 132 to be connected to the cassette, as shown in FIGS. 1 and 2, the connectors 160 allow dialysate to be pumped into and out of the cassette 112 during use.

Figure 5:
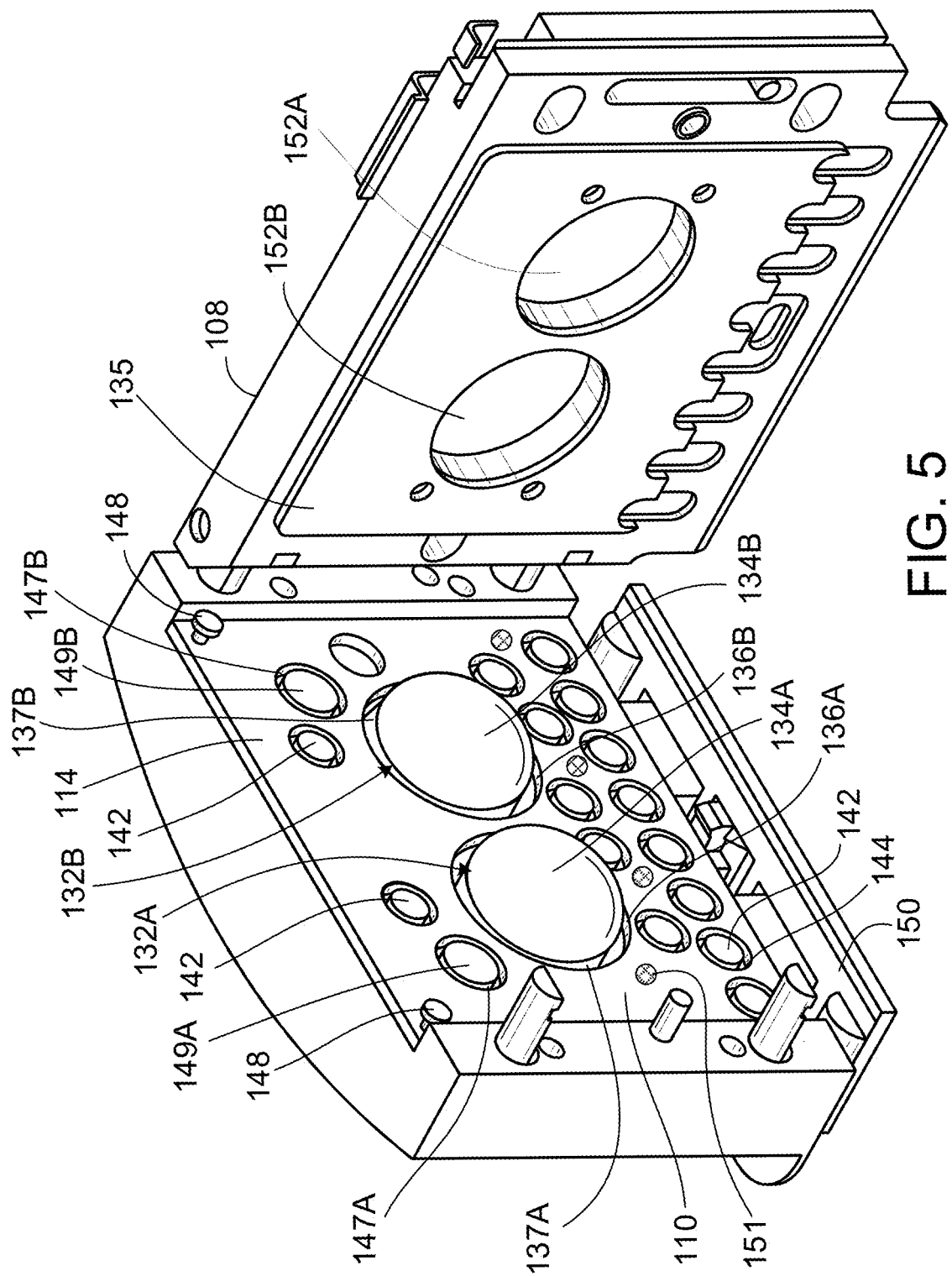
FIG. 5 is a perspective view of an open cassette compartment of the PD cycler of FIG. 1.

FIG. 5 shows a detailed view of the cassette interface 110 and the door 108 of the PD cycler 102. As shown, the PD cycler 102 includes pistons 132A, 132B with substantially hemispherical piston heads 134A, 134B that can be axially moved within piston access ports 136A, 136B formed in the cassette interface 110. The piston access ports 136A, 136B form annular passages 137A, 137B that surround the piston heads 134A, 134B and are in fluid communication with portions of the cassette membrane 140 overlying pump chambers 138A, 138B when the cassette 112 is disposed in the cassette compartment 114 of the PD cycler 102. As a result, vacuum pressure applied to the annular passages 137A, 137B during use of the PD cycler 102 can be used to draw the membrane 140 of the cassette 112 against the piston heads 134A, 134B.

Still referring to FIG. 5, the pistons 132A, 132B are coupled to motors that can be operated to move the piston heads 134A, 134B axially inward and outward within the piston access ports 136A, 136B. When the cassette 112 is positioned within the cassette compartment 114 with the door 108 closed, the piston heads 134A, 134B of the PD cycler 102 align with the pump chambers 138A, 138B of the cassette 112. As a result, the piston heads 134A, 134B can be moved in the direction of the cassette 112 to force the membrane 140 of the cassette 112 toward the rigid base 156, causing the volume defined by the pump chambers 138A, 138B to decrease and forcing dialysate out of the pump chambers 138A, 138B. The piston heads 134A, 134B can also be retracted away from the base 156 of the cassette 112. Portions of the cassette membrane 140 overlying the pump chambers 138A, 138B are drawn toward the piston heads 134A, 134B with vacuum force as the pistons heads 134A, 134B are retracted. In particular, the annular passages 137A, 137B surrounding the piston heads 134A, 134B (i.e., the portions of the piston access ports 136A, 136B that surround the piston heads 134A, 134B) can be used to apply a vacuum force to those portions of the membrane 140 overlying the pump chambers 138A, 138B. The piston access ports 136A, 136B are connected to a vacuum source (e.g., an air pump or vacuum reservoir) to allow the vacuum pressure to be applied to the membrane 140 of the cassette 112 via the annular passages 137A, 137B. As a result, the volume defined by the pump chambers 138A, 138B increases and dialysate is drawn into the pump chambers 138A, 138B as the piston heads 134A, 134B retract together with respective portions of the cassette membrane 140.

As shown in FIG. 5, the PD cycler 102 also includes multiple inflatable members 142 positioned within inflatable member access ports 144 in the cassette interface 110. The inflatable members 142 align with the depressible dome regions 146 of the cassette 112 when the cassette 112 is positioned within the cassette compartment 114. The inflatable members 142 are connected to fluid lines that act as conduits for applying positive pressure and/or vacuum pressure to the inflatable members 142 such that the inflatable members 142 can be inflated and deflated during use. While not all of the inflatable members 142 are labeled in FIG. 5, it should be understood that the PD cycler 102 includes an inflatable member associated with each of the depressible dome regions 146 of the cassette 112 (shown in FIG. 4). The inflatable members 142 act as valves to direct dialysate through the cassette 112 in a desired manner during use. In particular, the inflatable members 142 bulge outward beyond the surface of the cassette interface 110 and into contact with the depressible dome regions 146 of the cassette 112 when inflated, and retract into the inflatable member access ports 144 and out of contact with the cassette 112 when deflated. By inflating certain inflatable members 142 to depress their associated dome regions 146 on the cassette 112, certain fluid flow paths within the cassette 112 can be blocked off. Thus, dialysate can be pumped through the cassette 112 by actuating the piston heads 134A, 134B, and can be guided along desired flow paths within the cassette 112 by selectively inflating and deflating the inflatable members 142.

Still referring to FIG. 5, the cassette interface 110 also includes vacuum ports 151 that are connected to vacuum lines positioned within the housing of the PD cycler 102. The vacuum ports 151 allow vacuum pressure to be applied to the cassette membrane 140 when the cassette 112 is positioned adjacent to the cassette interface 110. Applying vacuum pressure to the membrane 140 through the vacuum ports 151 draws the membrane 140 toward the cassette interface 110, thereby forming a seal between the cassette interface 110 and the membrane 140.

The cassette interface 110 also includes pressure sensors 149A, 149B. These sensors can, for example, be solid state silicon diaphragm infusion pump force/pressure transducers. An example of such a transducer is Model 1865 made by Sensym Foxboro ICT. Output signals generated by the pressure sensors 149A, 149B are transmitted to a control unit (e.g., processor) 1090 (shown in FIG. 1) of the PD cycler 102 via a wired or wireless connection. When the cassette 112 is inserted into the cassette compartment 114, the pressure sensing chambers 153A, 153B (shown in FIG. 4) of the cassette 112 line up and are in contact with the pressure sensors 149A, 149B. These pressure sensing chambers 153A and 153B are connected directly to the pump chambers 138A and 138B, respectively, of the cassette 112 such that when dialysate moves into and out of the pump chambers 138A, 138B, the pressure sensors 149A, 149B can measure the pressure of the dialysate passing through the pressure sensing chambers 153A, 153B, and can thus detect the pressure of the dialysate in the associated pump chamber 138A, 138B. The cassette membrane 140 is drawn against the pressure sensors 149A, 149B using vacuum pressure. In particular, annular passages 147A, 147B that surround the pressure sensors 149A, 149B allow vacuum pressure to be applied to the cassette membrane 140. Drawing the cassette membrane 140 close to the pressure sensors 149A, 149B can improve the accuracy of the pressure readings detected by those sensors.

The door 108, as shown in FIG. 5, defines recesses 152A, 152B that substantially align with the piston heads 134A, 134B when the door 108 is in the closed position. When the cassette 112 is positioned within the cassette compartment 114, hollow projections that form the recessed regions 163A, 163B in the base 156 of the cassette 112 and cooperate with the membrane 140 to form the pump chambers 138A, 138B fit within the recesses 152A, 152B in the door 108. An inflatable pad 135 in the door 108 can be inflated during use to compress the cassette 112 between the door 108 and the cassette interface 110. With the pad 135 inflated, the portions of the door 108 forming the recesses 152A, 152B support the hollow projections of the base 156 of the cassette 112 and the planar surface of the door 108 supports the other regions of the base 156 of the cassette 112. The door 108 can counteract the forces applied by the piston heads 134A, 134B and the inflatable members 142 and thus allows the piston heads 134A, 134B to depress the portions of the cassette membrane 140 overlying the pump chambers 138A, 138B and similarly allows the inflatable members 142 to actuate the depressible dome regions 146 on the cassette 112.

The PD cycler 102 also includes a safety clamp 150, which serves to close all inlets to and outlets from the cassette, for example, in the case of a system error. As seen in FIG. 5, the safety clamp 150 is a bar arranged below the cassette compartment. The safety clamp 150 is spring biased to a closed position in which the bar is urged against an interior surface of the door 108. When in the closed position, the safety clamp 150 extends across all of the lines 126, 128, 130, 132 connected to the cassette 112, whereby all lines 126, 128, 130, 132 extending from the cassette 112 are crimped closed. During normal operation, the safety clamp 150 is retracted away from the door 108 using pneumatic pistons operated by the pneumatic system.

Figure 6:
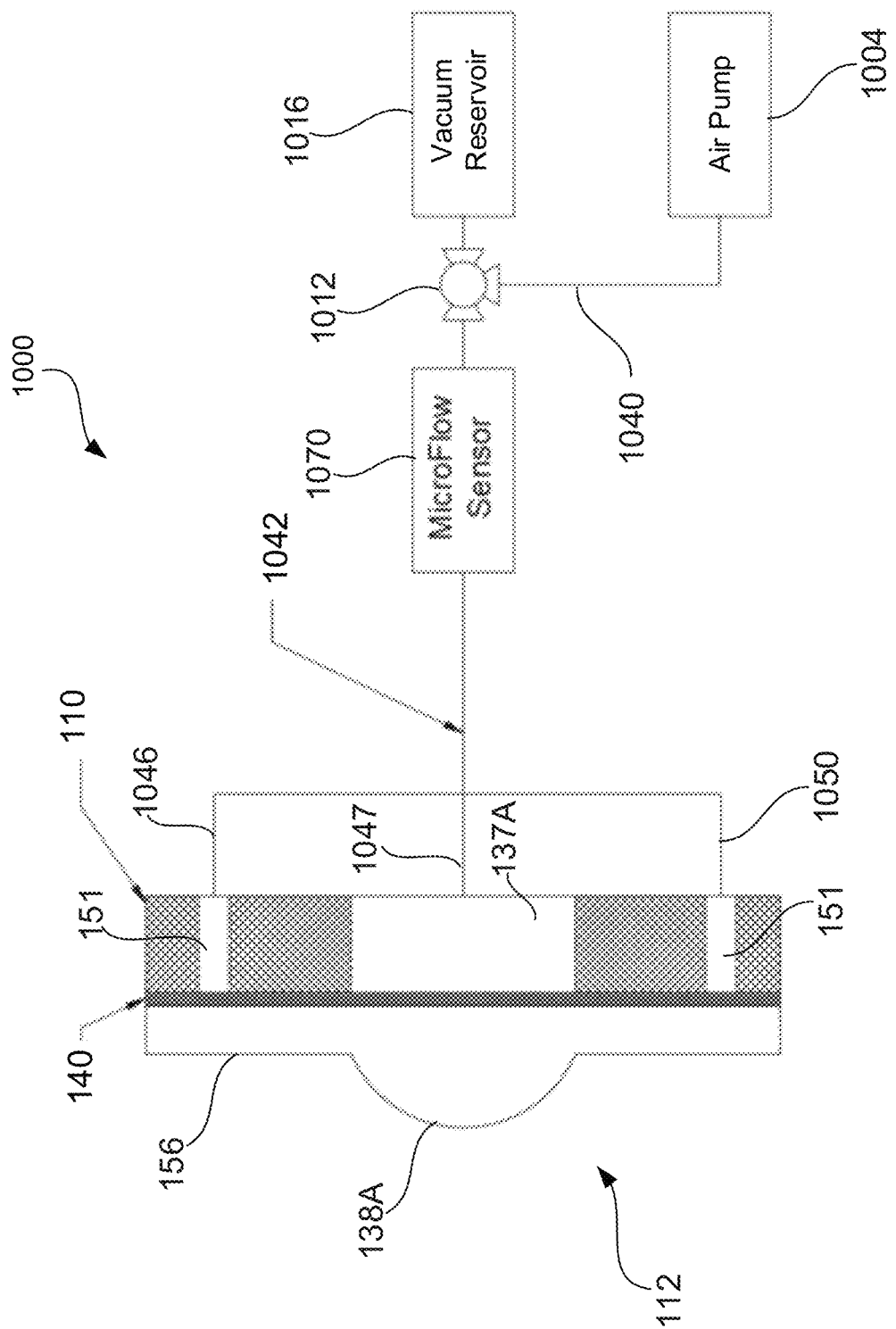
FIG. 6 is a cross sectional schematic illustration of an air distribution system of the PD cycler of FIG. 1 fluidly connected to the cassette of FIG. 2.

FIG. 6 is a cross sectional schematic of an air distribution system 1000 of the PD cycler 102 that is fluidly connected to the cassette 112. The air distribution system 1000 includes an air pump 1004 that is configured to generate positive air pressure or negative (vacuum) air pressure and can be used to apply that positive pressure or vacuum pressure to the annular passages 137A, 137B surrounding the piston heads 134A, 134B, to the inflatable members 142, to the vacuum ports 151, and/or to the annular passages 147A, 147B surrounding the pressure sensors 149A, 149B. The air pump 1004 is connected via air line(s) or tube(s) 1040 to a valve manifold 1012. The air line(s) 1040 can be used to connect to a vacuum outlet port of the air pump 1004 to supply vacuum pressure to the manifold 1012 and/or to a positive pressure outlet port of the air pump 1004 to supply positive pressure to the manifold 1012.

The manifold 1012 can include multiple valves that can be actuated to guide the positive and negative pressure received from the air pump 1004 in a desired manner through any of various different air lines 1042, 1046, 1047, 1050 connected to the manifold 1012. The valves of the manifold 1012 can, for example, be solenoid valves that are controlled by the control unit (e.g., processor) 1090 (shown in FIG. 1) of the PD cycler 102.

Positive air pressure or vacuum pressure can be delivered to the inflatable members 142 via one or more lines that connect(s) each of the inflatable members 142 to manifold 1012. For example, air pump 1004 can be used to supply positive pressure to the inflatable members 142 and inflate the inflatable members 142. Each inflatable member 142 can be connected to a separate pressure line and vacuum line. In some embodiments, positive pressure and vacuum pressure are distributed to each inflatable member 142 using only a single line connecting the manifold 1012 to that inflatable member 142. By controlling the pressure supplied to the inflatable valve members 142, each of the inflatable valve members 142 can be held in an inflated or a deflated state. As noted above, inflating and deflating the various inflatable members 142 can be used to control fluid flow through the cassette 112.

Air lines 1046 and 1050 extend between air line 1042 and the vacuum ports 151 formed in the cassette interface 110 of the PD cycler 102. Thus, air lines 1046 and 1050 can be used to supply vacuum pressure to the vacuum ports 151. As depicted in FIG. 6, the vacuum pressure applied to the vacuum ports 151 can be used to pull the membrane 140 of the cassette 112 against the cassette interface 110 of the PD cycler 102.

An end of air line 1042 opposite the manifold 1012 is connected to air lines (not shown) that are in fluid communication with the annular passages 147A, 147B surrounding chamber pressure sensors 149A, 149B. Supplying vacuum pressure to the annular passages 147A, 147B can help to ensure that the membrane 140 of the cassette 112 is pulled firmly against the pressure sensors 149A, 149B and can thus increase the accuracy of pressure measurements detected by those sensors.

An end of air line 1042 opposite the manifold 1012 is connected to the air line(s) 1047, which are in fluid communication with the annular passages 137A, 137B surrounding the piston heads 134A, 134B. As a result, vacuum pressure can be supplied to the annular passages 137A, 137B via the air line(s) 1047. This vacuum pressure can help secure the membrane 140 of the cassette 112 to the piston heads 134A, 134B as the piston heads 134A, 134B are reciprocated during use.

Positive pressure can be selectively applied (i.e., by controlling the valves of the manifold 1012) to the inflatable pad 135 in order to inflate the inflatable pad 135. For example, air pump 1004 can be used to provide positive pressure to the inflatable pad 135 in order to inflate the inflatable pad 135. In order to deflate the inflated pad 135, the pressure is exhausted to atmosphere (i.e., by controlling the valves of a manifold coupled to an air line coupled to the inflatable pad 135). The inflatable pad 135, as described above, can be used to compress the cassette 112 against the cassette interface 110 of the PD cycler 102, which can help ensure that the membrane 140 of the cassette 112 is held firmly in contact with the various components exposed on the surface of the cassette interface 110 of the PD cycler 102 during use.

The safety clamp 150 located on the PD cycler 102 along a lower edge of the cassette compartment receives vacuum pressure via an air line (not shown) fluidly coupled to the safety claim 150. Positive pressure can be selectively applied to the safety clamp 150 in order to retract the safety clamp away from the door 108 against the biasing force of a bias spring (not shown). In order to actuate the safety clamp 150, the pressure is exhausted to atmosphere (i.e., by controlling the valves of a manifold connected to the air line fluidly coupled to the safety clamp 150), permitting the bias spring to advance the safety clamp toward the door 108. The safety clamp 150, as described above, serves to close all inlets to and outlets from the cassette 112 in the case of a system error.

Still referring to FIG. 6, a vacuum reservoir 1016 is also connected to the air line 1042 via manifold 1012. The vacuum reservoir 1016 contains a supply of air maintained at a negative pressure (e.g., at a pressure of about −150 mbar to about −200 mbar). During use, valves of the manifold 1012 can be operated in a manner to pull a vacuum on the annular passages 137A, 137B via the air lines 1047. The vacuum reservoir 1016 can be used as an alternative to or in addition to the air pump 1004 in order to supply vacuum pressure to the annular passages 137A, 137B and vacuum ports 151 of the cassette interface 110. For example, the air pump 1004 is simply used in an intermittent fashion to ensure that the vacuum reservoir 1016 is maintained at a desired negative pressure, and the vacuum reservoir 1016 is used to apply negative pressure to the annular passages 137A, 137B. A vacuum pressure of about −150 mbar to about −200 mbar is typically applied to the annular passages 137A, 137B and thus to the portions of the cassette membrane 140 positioned adjacent those annular passages 137A, 137B. By utilizing the vacuum reservoir 1016 as a supplement to or substitute for the air pump 1004 during use, the time period during which the air pump 1004 needs to be operated during use can be reduced. This can advantageously reduce the noise associated with operating the air pump 1004.

A vacuum reservoir (e.g., vacuum reservoir 1016) can be operated in a manner similar to the vacuum reservoir 1016 to supply vacuum pressure to the inflatable members 142, the vacuum ports 151, and the annular passages 147A, 147B surrounding the pressure sensors 149A, 149B via air lines. A vacuum pressure of about −550 mbar can be applied to the inflatable members 142, the vacuum ports 151, and the annular passages 147A, 147B surrounding the pressure sensors 149A, 149B.

The air lines 1042, 1046, 1047, 1050 that are fluidly connected to the vacuum reservoir 1016 can be equipped with vacuum sensors that can detect vacuum pressure within those lines. Any of various different types of vacuum sensors capable of detecting the vacuum pressure within the air lines 1042, 1046, 1047, 1050 can be used. An example of a suitable vacuum sensor is the ASDX-15 force/pressure transducers available from Honeywell (Morristown, NJ). Other suitable vacuum sensors, including the Sensor Technics RXUP015 and the All Sensors 15 PSI-Dx-4V-MINI, can alternatively or additionally be used.

As depicted in FIG. 6, the air distribution system 1000 also includes a micro-flow sensor 1070 positioned along and fluidly coupled to the air line 1042 extending from the manifold 1012. The micro-flow sensor 1070 is configured to detect fluid flow along the air line 1042, which fluidly connects the vacuum ports 151 and annular passages 137A, 137B, 147A, 147B to the vacuum reservoir 1016. For example, as will be described in further detail herein, after all inlets to and outlets from the cassette 112 are closed (e.g., using clamp 150 and vacuum pressure is applied to the cassette membrane 140 using air pump 1004 and/or the vacuum reservoir 1016, the micro-flow sensor 1070 can be used to measure the rate of net fluid flow along air line 1042 in order to detect whether the cassette 112 contains one or more micro-leaks. The micro-flow sensor 1070 can detect net flow rates ranging from about 1.5 cc/min to about 10 cc/min. As will described in further detail herein, the micro-flow sensor 1070 can be communicatively coupled to a controller of the PD cycler 102 (e.g., control unit 1090) and flow measurements detected by the micro-flow sensor 1070 can be transmitted to the controller of the PD cycler 102 in real time. Any suitable micro-flow sensor 1070 can be used, such as HONEYWELL ZEPHYR™ digital airflow HAF series sensors.

A method of operating the PD cycler 102 will now be described. Before treatment, the door 108 of the PD cycler 102 is opened to expose the cassette interface 110, and the cassette 112 is positioned with its membrane 140 adjacent to the cassette interface 110. The cassette 112 is positioned such that the pump chambers 138A, 138B of the cassette 112 are aligned with the piston heads 134A, 134B, the depressible dome regions 146 of the cassette 112 are aligned with the inflatable members 142, and the pressure sensing chambers 153A, 153B of the cassette 112 are aligned with the pressure sensors 149A, 149B.

Referring also to FIG. 6, which schematically illustrates the air distribution system 1000 of the PD cycler 102, after loading the cassette 112 into the cassette compartment 114 of the PD cycler 102, positive pressure is supplied to the inflatable pad 135 in the door 108 of the PD cycler 102. In particular, positive pressure is supplied from the air pump 1004 to the inflatable pad 135. The positive pressure inflates the inflatable pad 135 to secure the cassette 112 within the cassette compartment 114 in a manner such that the membrane 140 of the cassette 112 is pressed firmly against the cassette interface 110 of the PD cycler 102.

In addition, vacuum pressure is supplied to the vacuum ports 151 to form a seal between the membrane 140 and the cassette interface 110. Vacuum pressure is also supplied to the annular passages 147A, 147B formed around the pressure sensors 149A, 149B to draw the membrane 140 against those pressure sensors 149A, 149B. The vacuum pressure is supplied from the air pump 1004 and/or the vacuum reservoir 1016 to the vacuum ports 151 and the annular passages 147A, 147B. The vacuum pressure is directed through the air lines 1042, 1046 and 1050 to the vacuum ports 151. Similarly, the vacuum pressure is directed through the air lines to the annular passages 147A, 147B surrounding the pressure sensors 149A, 149B.

Vacuum pressure is also applied to the annular passages 137A, 137B surrounding the piston heads 134A, 134B. The vacuum pressure is supplied from the air pump 1004 and/or the vacuum reservoir 1016 to the annular passages 137A, 137B via the air lines 1042 and 1047. With the cassette 112 loaded into the cassette compartment 114, the membrane 140 of the cassette 112 covers the annular passages 137A, 137B. As a result, when the piston heads 134A, 134B are retracted away from the cassette 112 during use, the vacuum pressure applied to the membrane 140 via the annular passages 137A, 137B causes the portions of the membrane 140 overlying the piston heads 134A, 134B to be drawn toward the cassette interface 110 in unison with the retracting piston heads 134A, 134B. As a result, the volume defined by the pump chambers 138A, 138B increases, and, depending on the state of the inflatable members 142, dialysate can be drawn into the pump chambers 138A, 138B as the piston heads 134A, 134B retract together with respective portions of the membrane 140. Similarly, depending on the state of the various inflatable members 142, as the piston heads 134A, 134B are advanced, the volume of the pump chambers 138A, 138B decreases, forcing dialysate from the pump chambers 138A, 138B.

As the pistons 132A, 132B of the PD cycler 102 reciprocate, each of the inflatable members 142 is either inflated or deflated to control the flow of dialysate through the cassette 112. To inflate the inflatable members 142, positive pressure is applied from the air pump 1004 to an inflatable member valve manifold. The valves of the inflatable member valve manifold are operated in a manner to deliver the positive pressure only to those inflatable members 142 that are to be or remain inflated. To deflate the inflatable members 142, vacuum pressure is supplied from the air pump 1004 and/or the vacuum reservoir 1016 to the inflatable member valve manifold. The valves of the inflatable member valve manifold are operated in a manner to deliver the vacuum pressure only to those inflatable members 142 that are to be or remain deflated. Signals related to the pressure within the air line coupled to the inflatable members 142 are transmitted from a vacuum sensor a to the control unit 1090 of the PD cycler 102 throughout treatment.

In rare instances, the flexible membrane 140 of the PD fluid cassette 112 may have micro-leaks caused by small pin-holes or tears in the cassette 112. The holes and tears that result in micro-leaks can be caused, for example, by damage during handling. Micro-leaks are leaks that are typically too small to be detected using pressure decay tests, as the pressure decay resulting from micro-leaks is typically below detectable thresholds. In some implementations, a micro-leak includes leaks caused by an opening in the cassette membrane 140 with a diameter of 0.005 inches or less. In some implementations, micro-leaks include leaks that allow a fluid to flow at a rate between about 1.55 cc/min and 10 cc/min along a fluid line coupled to the cassette (e.g., along fluid line 1042) when a vacuum pressure in a range of about 500 mbar to about 550 mbar is applied to the cassette membrane 140 at a temperature ranging from about 18° C. to about 38° C. In some implementations, the vacuum pressure is applied to the cassette membrane 140 with only air flowing through the cassette 112 and without any other fluids (such as a liquid) flowing through the cassette 112.

Although the holes or tears that form micro-leaks are initially small, those holes or tears can develop into larger holes or tears during dialysis treatment, and these larger holes or tears result in larger leaks that can allow significant amounts of dialysate to leak through the flexible membrane 140 and enter the mechanical and pneumatic systems of the PD cycler 102. Dialysate leaks can render the PD cycler inoperable.

In order to avoid using a potentially leaky PD fluid cassette 112, the PD cycler 102 can perform a cassette micro-leak detection test on the PD fluid cassette 112 prior to use (e.g., immediately prior to peritoneal dialysis treatment). In some cases, methods used by the PD cycler 102 to detect micro-leaks in the cassette 112 include using air as the test fluid so that if a micro-leak is detected, liquid is prevented from entering the mechanical and pneumatic systems of the PD cycler 102.

Figure 7:
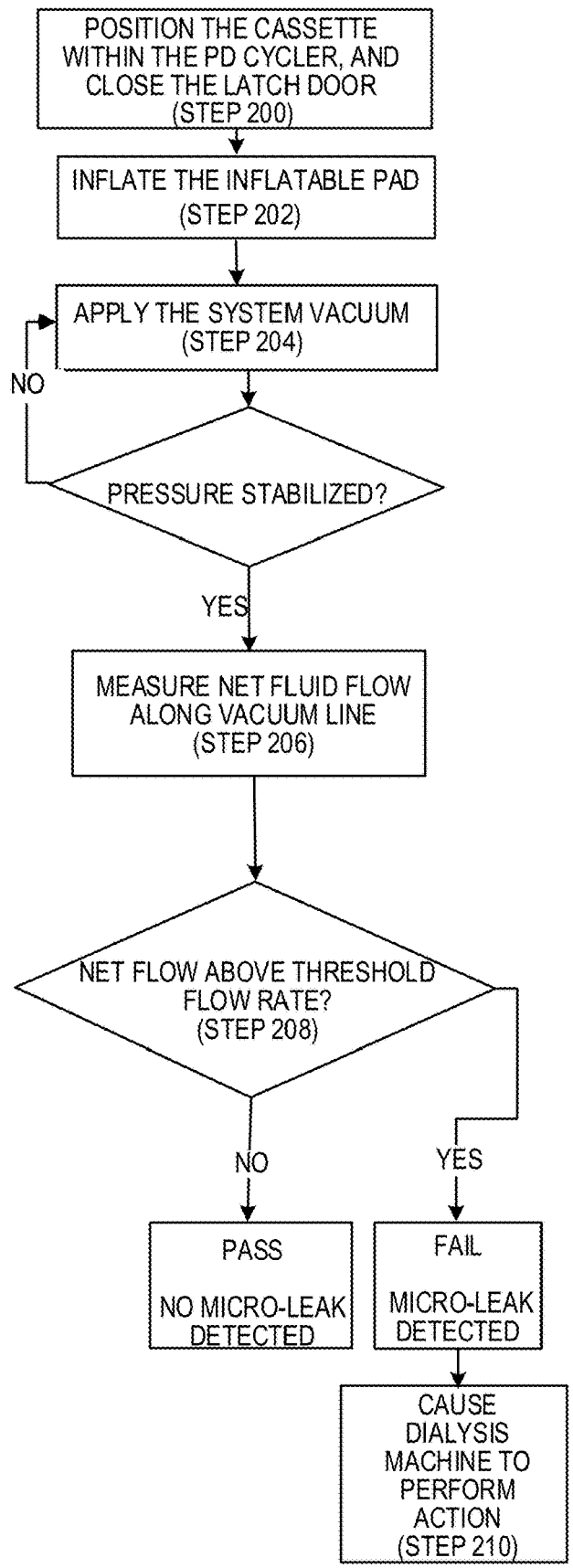
FIG. 7 is a flow chart that illustrates a method for detecting micro-leaks in a PD cassette fluidly coupled to a PD cycler.

Referring to FIGS. 6 and 7, a method of detecting micro-leaks in the PD fluid cassette 112 will now be described.

Prior to starting a dialysis treatment, the PD fluid cassette 112 is positioned within the PD cycler 102 in the manner described above, e.g., in a manner consistent with normal use. The door 108 of the PD cycler 102 is then closed and latched (Step 200).

Once the door 108 is closed and latched, the inflatable pad 135 within the door 108 is inflated (Step 202), and a system vacuum is applied to the cassette flexible membrane 140 (Step 204). For example, vacuum pressure is applied to the membrane 140 through the vacuum ports 151, the annular passages 137A, 137B surrounding the piston access ports 136A, 136B, and the annular passages 147A, 147B surrounding the pressure sensors 149A, 149B. In some implementations, the vacuum pressure is applied to the membrane 140 using the vacuum reservoir 1016. In some implementations, a vacuum pressure is applied to the membrane 140 using the air pump 1004. During application of the vacuum pressure, the inflatable members 142 of the cassette interface are collapsed and all flow paths through the cassette 112 are open to allow air to flow freely throughout the cassette 112 and towards the vacuum reservoir 1016.

Vacuum pressure is continuously applied to the membrane 140 until the membrane 140 forms a seal with the cassette interface 110 and the pressure within the cassette 112 and the air distribution system 1000 has stabilized. In some implementations, a vacuum pressure in a range of about 500 mbars to about 550 mbars is applied to the membrane 140 at a temperature in a range of about 18° C. to about 38° C. in order to test the membrane 140 for micro-leaks.

Once a pressure within the range of about 500 mbar to about 550 mbar has been applied to the membrane 140 and a predetermined stabilization period ranging from about 8 seconds to about 12 seconds has elapsed following the vacuum pressure reaching a range of about 500 mbar to about 550, micro-flow sensor 1070 begins to monitor the rate of net fluid flow along the air line 1042 fluidly coupling the cassette 112 and the vacuum reservoir 1016 (Step 206). The micro-flow sensor 1070 can detect net flow rates ranging from about 1.5 cc/min to about 10 cc/min. In some implementations, the stabilization period is ten seconds such that the micro-flow sensor begins monitoring fluid flow along the air line 1042 ten seconds after the vacuum pressure applied to the membrane 140 reaches a range of about 500 mbar to about 550 mbar. In some implementations, the micro-flow sensor 1070 measures fluid flow along air line 1042 for a predetermined amount of time (e.g., for a predetermined testing period) ranging from about 8 seconds to about 12 seconds.

In some implementations, the fluid flow measurements captured by the micro-flow sensor 1070 are transmitted to the control unit 1090 of the PD cycler 102 via a wired or wireless connection for processing of the sensor data. In some implementations, the fluid flow measurements captured by the micro-flow sensor 1070 are transmitted to the control unit of the PD cycler 102 in real time.

Based on the rate of net fluid flow between the cassette 112 and the vacuum reservoir 1016 measured by the micro-flow sensor during the testing period, the control unit 1090 determines whether the rate of net fluid flow exceeds a threshold flow rate (Step 208). In some implementations, the threshold flow rate ranges from about 1.25 cc/min to about 1.75 cc/min when a vacuum pressure ranging from about 500 mbar to about 550 mbar is applied to the membrane 140 at a temperature ranging from about 18° C. to about 38° C.

If it is determined that the rate of net fluid flow along the air line 1042 between the cassette 112 and the vacuum reservoir 1016 during the testing period is below the threshold flow rate, the control unit 1090 identifies the cassette 112 as not containing a micro-leak and as passing the micro-leak test. In some implementations, in response to the control unit 1090 determining that the rate of net fluid flow along the air line 1042 between the cassette 112 and the vacuum reservoir 1016 is below the threshold flow rate, the control unit 1090 controls the PD cycler 102 to a generate an audible or visual message indicating that the cassette 112 has passed testing and instructs an operator of the cycler 102 to proceed with treatment (e.g., by connecting the patient to the cycler 102 and/or opening the valves along one or more solution line 126, 128 to the dialysate bags 122 and/or heater bag 124). In some implementations, in response to the control until 1090 determining that the rate of net fluid flow along the air line 1042 between the cassette 112 and the vacuum reservoir 1016 is below the threshold flow rate, the control unit 1090 controls the PD cycler 102 to automatically begin treatment. For example, in response to the control until 1090 determining that the rate of net fluid flow along the air line 1042 between the cassette 112 and the vacuum reservoir 1016 is below the threshold flow rate, the control unit 1090 can control the air pump 1004 and/or vacuum reservoir 1016 to stop applying vacuum pressure to the cassette 112, and once the vacuum pressure is released, can control the PD cycler 102 to proceed with the next step of operation in the treatment.

If it is determined that the rate of net fluid flow along the air line 1042 between the cassette 112 and the vacuum reservoir 1016 is above the threshold flow rate, the control unit 1090 identifies the cassette 112 as containing a micro-leak and failing the micro-leak test. For example, if the membrane 140 of the cassette 112 includes a hole or tear with a diameter of about 0.003 inches to about 0.005 inches (and thus includes a micro-leak), small amounts of fluid will be able to flow through the membrane 140 when the membrane is under vacuum pressure. As a result, when vacuum pressure is applied by the vacuum reservoir 1016 to a membrane 140 with a micro-leak, it is anticipated that small amounts of air will flow from the cassette 112 through the membrane 140 towards the vacuum reservoir 1016 in order to maintain the pressure within the system 1000 and maintain the seal between the membrane 140 and the cassette interface 110. As a result, net fluid flow above a threshold flow rate from the cassette 112 to the vacuum reservoir 1016 will occur and will be detected by the micro-flow sensor 1070 when vacuum pressure is applied to a cassette 112 with a micro-leak. In some implementations, the amount of flow between the cassette 112 with a micro-leak and the vacuum reservoir 1016 is an amount that is below the detection threshold of standard flow sensors and is not detectable using standard pressure decay tests.

In some implementations, in response to detecting that the rate of net fluid flow between the cassette 112 and the vacuum reservoir 1016 is above a threshold flow rate, the control unit 1090 of the PD cycler 102 causes the PD cycler 102 to perform one or more actions (Step 210). For example, in response to detecting that the rate of net fluid flow between the cassette 112 and the vacuum reservoir 1016 is above a threshold flow rate, and thus the cassette 112 contains a micro-leak, the PD cycler 102 generates an audible indication of the micro-leak (e.g., an audible warning emitted by speakers of the PD cycler 102), a visual indication of the micro-leak (e.g., a visual warning displayed on the screen 118 of the PD cycler 102), and/or a tactile indication (e.g., vibration of one or more components of the PD cycler 102).

In some implementations, in response to detecting that the rate of net fluid flow between the cassette 112 and the vacuum reservoir 1016 is above a threshold flow rate, and thus the cassette 112 contains a micro-leak, the PD cycler 102 is disabled and prevented from performing treatments until the defective medical fluid cassette 112 is replaced with a new medical fluid cassette that does not contain a micro-leak. For example, in response to detecting that the rate of net fluid flow between the cassette 112 and the vacuum reservoir 1016 during the testing period is above a threshold flow rate, the control unit 1090 of the PD cycler 102 can control the screen 118 of the PD cycler 102 to display a message requiring the operator to press a button (for example, one of control buttons 120 or an indicator button displayed on the touch screen 118) to confirm that the cassette with the micro-leak has been removed and new a medical fluid cassette has been inserted into the cycler 102. In some implementations, the PD cycler 102 includes a detector, such as an RFID reader or a barcode reader, positioned on the PD cycler 102 to read a corresponding tag on a medical fluid cassette properly inserted in the cassette compartment 114 of the PD cycler 102. The detector can be used to confirm that a new medical fluid cassette has been inserted into the PD cycler 102, for example, by identifying that the new medical fluid cassette currently inserted into the cassette compartment 114 has a different tag than the medical fluid cassette 112 containing a micro-leak.

Once the control unit 1090 determines that the defective cassette 112 has been replaced with a new cassette, the control unit 1090 can control the PD cycler 102 to test the new cassette 112 for micro-leaks using the above described method (e.g., by performing steps 200-210 on the new cassette). If, after re-performing micro-leak testing (e.g., performing steps 200-208) following insertion of a new cassette, it is determined that the rate of net fluid flow between the new cassette and the vacuum reservoir 1016 during the testing period is below a threshold flow rate, this indicates that the defective cassette 112 has been replaced with a new, non-defective cassette and treatment can proceed. However, if after re-performing micro-leak testing (e.g., steps 200-210), it is determined that the rate of net fluid flow between the cassette 112 and the vacuum reservoir 1016 during the testing period is above a threshold flow rate, this indicates that the defective cassette 112 has not been replaced or that the new cassette also contains a micro-leak, and the PD cycler 102 is disabled and prevented from performing treatments until it is detected that the PD cycler 102 is coupled to a medical fluid cassette that does not contain a micro-leak, as determined based on the micro-leak testing process described above. In some implementations, the micro-leak detection test described above with reference to steps 200-208 is performed each time the controller 1090 detects that a new cassette has been inserted into the PD cycler 102.

If treatment was initiated prior to detecting that the cassette 112 includes a micro-leak, the PD cycler 102 can be controlled to terminate treatment in response to determining that the rate of net fluid flow between the cassette 112 and the vacuum reservoir 1016 is above a threshold rate during the testing period.

In some implementations, in response to detecting that the rate of net fluid flow between the cassette 112 and the vacuum reservoir 1016 during the testing period is above a threshold flow rate, the control unit 1090 determines whether the net fluid flow rate exceeds an upper boundary. For example, if the rate of net fluid flow between the cassette 112 and the vacuum reservoir 1016 exceeds a particular flow rate (e.g., an upper boundary flow rate) when a vacuum pressure in a range of about 500 mbar to about 550 mbar is applied to the membrane 140 of the cassette 112 at a temperature ranging from about 18° C. to about 38° C., it can be determined that the cassette 112 has already developed a full leak, rather than a smaller micro-leak. In some implementations, in response to detecting that film 140 has a full leak, the PD cycler 102 is disabled from providing treatment until the cycler 102 has been serviced. For example, in response to the control unit 1090 determining that the film 140 has a full leak, the control unit 1090 disables the PD cycler 102 from performing treatment until a service code indicating that the PD cycler 102 has been serviced is provided to the PD cycler 102 by an operator. In some implementations, the PD cycler 102 generates an audible or visual warning indicating to an operator that the PD cycler 102 requires service in response to detecting that the film 140 has a full leak. In some implementations, the PD cycler 102 generates an audible, visual, and/or tactile warning indicating to an operator that the film 140 has a leak and must be replaced with a new cassette.

While the above-described micro-leak detection method is conducted with the PD fluid cassette 112 coupled to the PD cycler 102, other testing arrangements can be used for detecting micro-leaks within a PD fluid cassette 112. For example, referring to FIGS. 8 and 9, an alternate system 400 and method for testing a PD fluid cassette 112 for micro-leaks that can be performed without coupling the cassette to a PD cycler 102 (e.g., during the process of manufacturing the cassette 112) will now be described.

Figure 8:
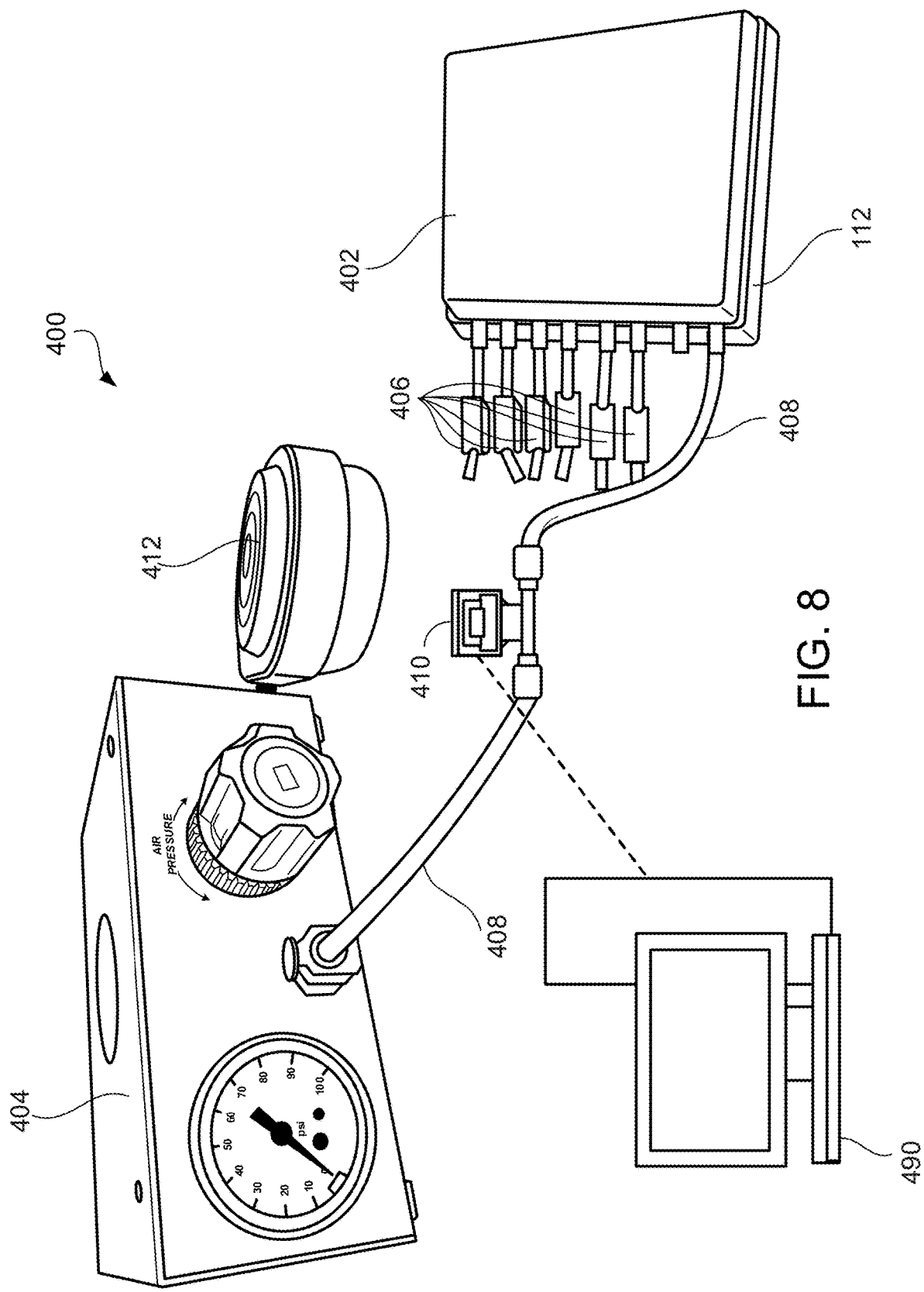
FIG. 8 is a schematic illustration of an example system for testing a PD cassette for micro-leaks.
Figure 9:
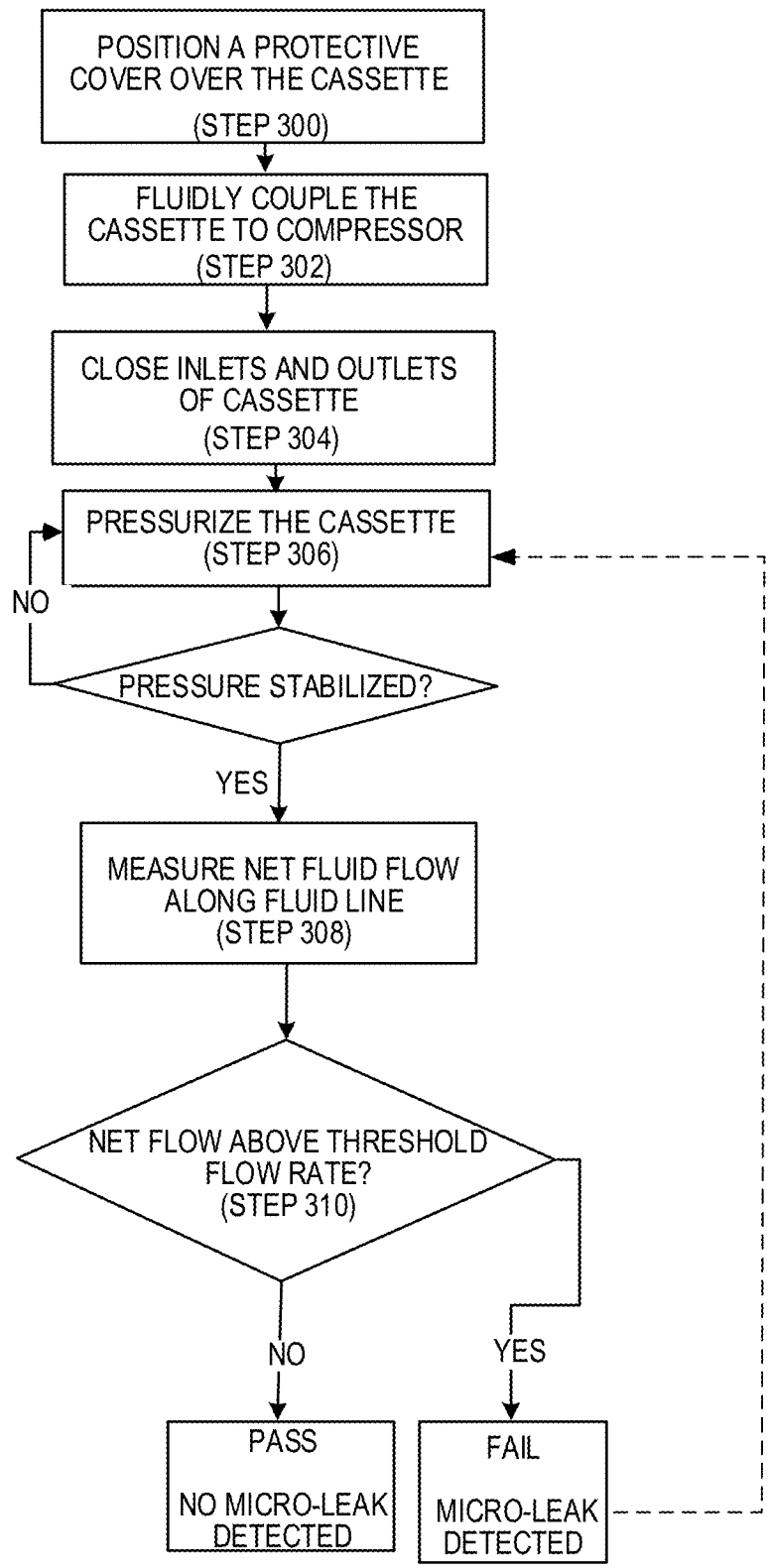
FIG. 9 is a flow chart that illustrates a method for testing a PD cassette for micro-leaks using the system of FIG. 8.

Referring to FIGS. 8 and 9, in order to test the PD fluid cassette 112 without coupling the cassette 112 to a PD cycler, a protective cover 402 is positioned over the PD fluid cassette 112 (Step 300), the cassette 112 is fluidly coupled to a pressure reservoir (Step 302), and all other inlets and outlets of the cassette are closed (e.g., using clamps 406) (Step 304).

The protective cover 402 is made of a porous material with a stiffness that exceeds the stiffness of the membrane 140 of the cassette 112. In some implementations, the protective cover 402 is formed of a porous polymer material, such as a woven polymer material. As will be described in further detail herein, during micro-leak testing, the cassette 112 is pressurized using the pressure reservoir 404. By covering the cassette 112 during testing with a protective cover 402 having a stiffness greater than the stiffness of the membrane 140, overexpansion of the cassette 112 that could result in tears or rupture of the membrane 140 of the cassette 112 is prevented. In addition, by limiting the expansion of the cassette membrane 140, the protective cover 402 allows for the pressure within the cassette 112 to stabilize.

By covering the cassette 112 during testing with a protective cover 402 that is porous, air leaking out of the cassette 112 (e.g., due to a micro-leak in the membrane 140) can be vented to the atmosphere. As a result, if the membrane 140 includes a micro-leak, additional air will be need to be provided to the cassette to maintain the pressure within the cassette 112, and this flow of additional air into the cassette can be used to identify a micro-leak, as will described in further detail herein.

Once the protective cover 402 is positioned over the PD fluid cassette 112, the cassette 112 is fluidly coupled to the pressure reservoir 404, and all other inlets and outlets of the cassette 112 are closed, pressurized air is provided from the air pressure reservoir 404 to the cassette 112 in order to pressurize the cassette 112 (Step 306). For example, an air compressor 412 fluidly coupled to the pressure reservoir 404 can pump air to the pressure reservoir 404 to pressurize the pressure reservoir 404. As a result, when the cassette 112 is fluidly coupled to the pressure reservoir 404 via air line 408, air flows from the pressure reservoir 404 to the cassette 112 and fills the fluid pathways 158 of the cassette 112 with air to pressurize the cassette 112. As the cassette 112 fills with pressurized air provided by the pressure reservoir 404, the membrane 140 of the cassette allows the fluid pathways of the cassette 112 to expand as they are filled with air. The protective cover 402 over the cassette 112 limits the expansion of the membrane 140 to prevent tears or rupture of the membrane. Air continues to flow from the pressure reservoir 404 to the cassette 112 until the membrane 140 is fully expanded within the protective cover 402 and the pressure within the cassette 112 and the pressure reservoir 404 stabilizes. In some implementations, a pressure in a range of about 550 mbar to about 1000 mbar is applied to the membrane 140 of the cassette 112 when the cassette 112 is pressurized using the pressure reservoir 404.

Once the cassette 112 has been pressurized and a predetermined stabilization period ranging from about 8 seconds to about 12 seconds has elapsed after the target pressure within the cassette 112 has been reached, the rate of net fluid flow along the air line 408 between the cassette 112 and the pressure reservoir 404 is measured by a micro-flow sensor 410 (Step 308). In some implementations, the stabilization period is ten seconds such that the micro-flow sensor 410 begins monitoring fluid flow along the air line 408 ten seconds after the pressure applied to the cassette 112 has reached a target pressure range. As can be seen in FIG. 8, the micro-flow sensor 410 is fluidly coupled to the air line 408 and is configured to detect fluid flow along the air line 408 fluidly connecting the cassette 112 to the pressure reservoir 404. For example, after pressurizing the cassette membrane 140 using the pressure reservoir 404, the micro-flow sensor 410 is used to measure the rate of net fluid flow along air line 408 in order to detect whether the cassette 112 contains one or more micro-leaks. The micro-flow sensor 410 can detect flow rates ranging from about 1.5 cc/min to about 10 cc/min. In some implementations, after the pressure within the cassette 112 and the predetermined stabilization period has elapsed, the micro-flow sensor 410 measures the rate of net fluid flow along air line 408 for a predetermined amount of time (e.g., a predetermined testing period) ranging from about 8 seconds to about 12 seconds.

The fluid flow measurements captured by the micro-flow sensor 410 are transmitted to a computing device 490 of the manufacturing system 400 via a wired or wireless connection. In some implementations, the fluid flow measurements captured by the micro-flow sensor 410 are transmitted from the micro-flow sensor 410 to the computing device 490 in real time.

Based on the rate of net fluid flow between the cassette 112 and the pressure reservoir 404 measured by the micro-flow sensor 410 during the testing period, the computing device 490 determines whether the rate of net fluid flow during the testing period exceeds a threshold amount of flow (Step 310). In some implementations, the threshold flow rate ranges from about 1.25 cc/min to about 1.75 cc/min when a pressure in a range of about 550 mbar to about 1000 mbar is applied to the membrane 140 of the cassette 112 at an ambient temperature (e.g., about 18° C. to about 28° C.). In some implementations, the air pressure is applied to the cassette 112 without any other fluids (such as liquid) flowing through the cassette 112.

If the computing device 490 determines that the rate of net fluid flow along the air line 408 between the cassette 112 and the pressure reservoir 404 during the testing period is below the threshold flow rate, the computing device 490 identifies the cassette 112 as not containing a micro-leak and passing the micro-leak test.

If it is determined that the rate of net fluid flow during the testing period along the air line 408 between the cassette 112 and the pressure reservoir 404 is above the threshold flow rate, the computing device 490 identifies the cassette 112 as containing a micro-leak and failing the micro-leak test. For example, if the membrane 140 of the cassette 112 includes a hole or tear with a diameter of about 0.003 inches to about 0.005 inches, small amounts of fluid will be able to flow through the membrane 140 (i.e., a micro-leak can form). As a result, small amounts of air will flow from the cassette 112 through the membrane 140 and the porous protective cover 402 and the pressure within the cassette 112 will lower. In response, small amounts of air will flow from the pressure reservoir 404 towards the cassette 112 in order to maintain the pressure within the cassette 112. As a result, net fluid flow above a threshold flow rate from the pressure reservoir 404 to the cassette 112 will occur and will be detected by the micro-flow sensor 410. In some implementations, the amount of fluid flow between the pressure reservoir 404 and a cassette 112 having a micro-leak is an amount that is below the detection threshold of standard flow sensors and is not detectable using standard pressure decay tests.

In some implementations, in response to the computing device 490 detecting that the rate of net fluid flow between the cassette 112 and the pressure reservoir 404 is above a threshold flow rate, and thus that the cassette 112 contains a micro-leak, the cassette 112 is tested a second time to confirm the presence of a micro-leak. For example, the cassette 112 can be re-pressurized by the pressure reservoir 404 and the rate of net fluid flow along the air line 408 between the cassette 112 and the pressure reservoir can be measured during a second testing period by the micro-flow sensor 410.

In some implementations, if computing device 490 determines that the rate of net fluid flow detected by the micro-flow sensor 410 during both the first testing period and the second testing period is above the threshold flow rate, the computing device 490 causes the manufacturing system 400 to mark cassette 112 as defective. For example, in response to determining that the rate of net fluid flow between the cassette 112 and the pressure reservoir 404 is above a threshold flow rate, the computing device 490 can control the manufacturing system 400 to divert the cassette 112 to a bin for collecting defective cassettes. In some implementations, in response to determining that the rate of net fluid flow between the cassette 112 and the pressure reservoir 404 is above a threshold flow rate, the computing device 490 causes the manufacturing system 400 to apply a "defective" stamp or label to the cassette 112. In some implementations, in response to determining that the rate of net fluid flow detected by the micro-flow sensor 410 between the cassette 112 and the pressure reservoir 404 is above a threshold flow rate, the computing device 490 causes the manufacturing system 400 to destroy the defective cassette 112. In some implementations, in response to determining that the rate of net fluid flow between the cassette 112 and the pressure reservoir 404 is above a threshold flow rate, the computing device 490 causes the manufacturing system 400 provide an audible and/or visual warning to an operator to indicate that the cassette 112 is defective.

In some implementations, in response to detecting that the rate of net fluid flow between the cassette 112 and the pressure reservoir 404 is above a threshold flow rate, the computing device 490 determines whether the net fluid flow exceeds a particular flow rate (e.g., an upper boundary rate). For example, if the rate of net flow between the cassette 112 and the pressure reservoir 404 during the testing period exceeds an upper boundary flow rate, it can be determined that the cassette 112 has already developed a full leak that is larger than a micro-leak. In some implementations, in response to determining that the film 140 has a full leak, the computing device 490 can control the manufacturing system 400 to divert the cassette 112 to a bin for collecting defective cassettes. In some implementations, the computing device 490 causes the manufacturing system 400 to apply a "defective" stamp or label to the cassette 112 in response to determining that the film 140 has a full leak. In some implementations, the computing device 490 causes the manufacturing system 400 to destroy the defective cassette 112 in response to determining that the film 140 has a full leak. In some implementations, in response to determining that the film 140 has a full leak, the computing device 490 causes the manufacturing system 400 provide an audible and/or visual warning indicating to an operator that the cassette 112 is defective.

EXAMPLE

Figure 10:
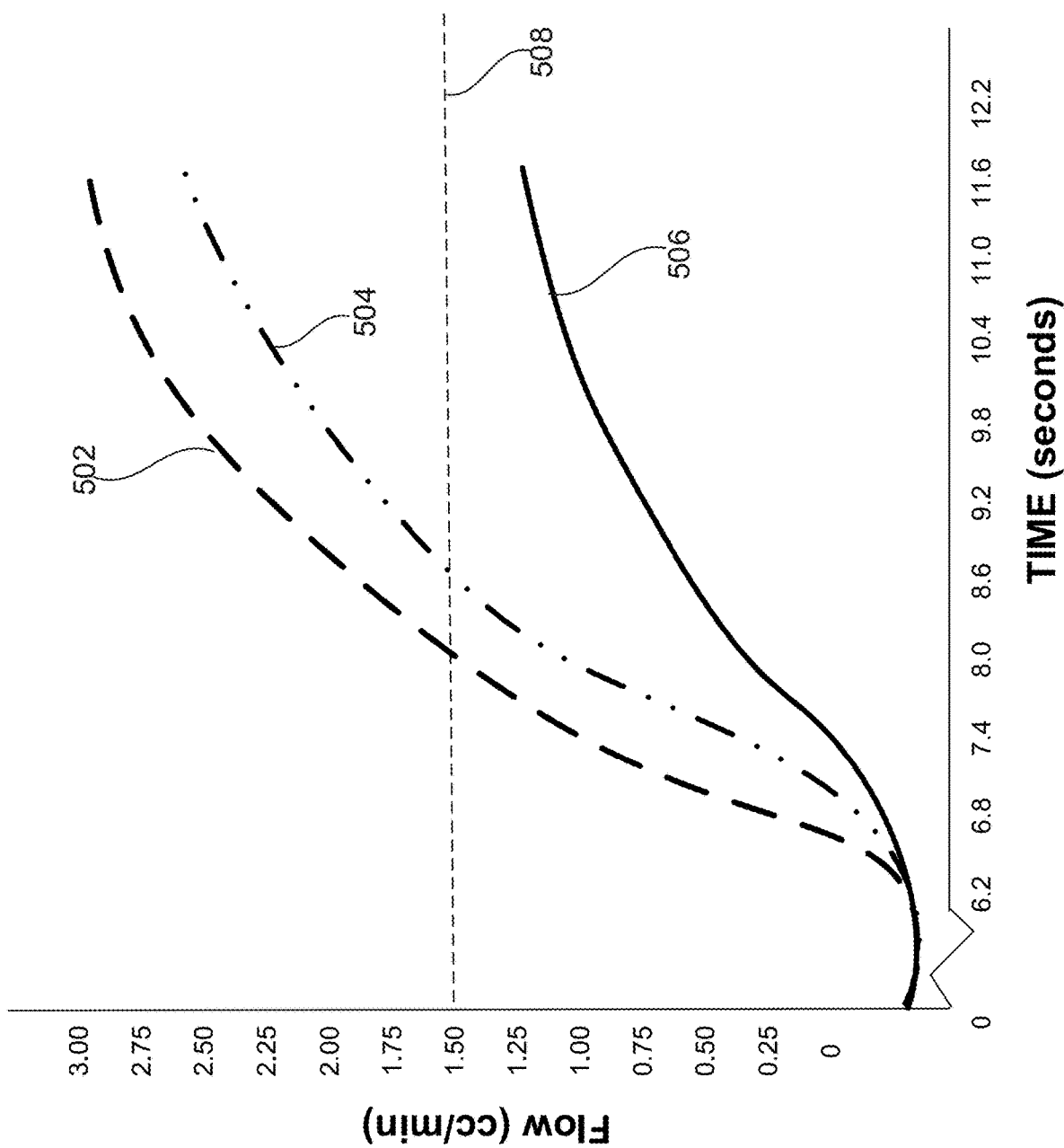
FIG. 10 is an example chart depicting the net fluid flow measured between a pressure reservoir and three PD cassettes during micro-leak testing.

FIG. 10 depicts example net flow rates measured for three medical fluid cassettes (e.g., similar to PD fluid cassette 112 of FIG. 1) using the above-described micro-leak testing methods. The net fluid flow measurements 502, 504, 506 represent the rate of net fluid flow between a respective fluid cassette and a pressure reservoir coupled to the respective cassette (e.g., pressure reservoir 404) following pressurization of the respective cassette. A first line 502 represents the rate of net fluid flow between the pressure reservoir and a first cassette having a hole through the membrane of the first cassette that is 0.005 inches in diameter, a second line 504 represents the rate of net fluid flow measured between the pressure reservoir and a second cassette having a hole through the membrane of the second cassette that is 0.003 inches in diameter, and a third line 506 represents the rate of net fluid flow between the pressure reservoir and a third cassette without any holes in the membrane of the third cassette.

The net fluid flow measurements 502, 504, 506 depicted in FIG. 10 were captured by a micro-flow sensor (e.g. micro-flow sensors 1070 and 410 of FIGS. 6 and 8, respectively) fluidly coupled to an air line connecting the respective cassette to the pressure reservoir. For example, each of the cassettes was pressurized with positive air pressure from a pressure reservoir to about 10 psi. Once each cassette was pressurized to about 10 psi and a 10 second stabilization period had elapsed following pressurization, the rate of net fluid flow between the respective cassette and the pressure reservoir was measured using a micro-flow sensor in order to capture the net fluid flow measurements 502, 504, 506 depicted in FIG. 10. The net fluid flow measurements 502, 504, 506 were each captured over a testing period of 12 seconds following pressurization of the respective cassettes and completion of the stabilization period.

A threshold flow rate 508 for detecting a micro-leak was set at 1.50 cc/min. As can be seen in FIG. 10, the rate of net fluid flow 502 measured for the cassette having the 0.005 inch diameter hole reached about 2.8 cc/min in 12 seconds, the rate of net fluid flow 504 measured for the cassette having the 0.003 inch diameter hole reached about 2.3 cc/min in 12 seconds, and the rate of net fluid flow 506 measured for the cassette without any holes reached about 1.2 cc/min in 12 seconds. As such, the rate of net fluid flow 502, 504 between the pressure reservoir and the first and second cassettes having holes of 0.005 inch and 0.0003 inch diameters, respectively, exceeded the threshold flow rate 508, indicating that the first and second cassettes each contained a micro-leak. Conversely, the rate of net fluid flow 506 between the pressure reservoir and third cassette without any holes did not exceed the threshold flow rate 508, indicating that the third cassette did not have any micro-leaks.

As discussed above, micro-leaks include leaks that typically cannot be detected using pressure decay tests, and the holes or tears that form micro-leaks can develop into larger holes or tears during dialysis treatment that result in larger leaks that can render the PD cycler inoperable. As such, by detecting the micro-leaks in the first and second cassette, the dialysis treatment can be stopped and/or the cassettes can be discarded prior to development of a leak that could cause damage to the PD cycler.

While certain embodiments have been described above, other embodiments are possible.

For example, while testing the cassette 112 for micro-leaks has been described as being performed prior to treatment, the cassette 112 can be tested for micro-leaks during treatment. For example, to test the membrane 140 of the cassette 112 for a micro-leak during treatment, the treatment is paused by stopping the motors coupled to the pistons 132A, 132B of the PD cycler 102, vacuum pressure is applied to the cassette 112, and steps 204-210 of the testing method described above in reference to FIG. 7 is performed. In some implementations, if a micro-leak in the cassette 112 is detected during treatment, a warning is generated by the PD cycler 102 and/or the PD cycler 102 is controlled to stop performing treatment. In some implementations, if based on the micro-leak test, it is determined that no micro-leak is present, the motors coupled to the pistons 132A, 132B of the cycler and be restarted and the treatment can proceed. In some implementations, micro-leak testing is performed on the cassette multiple times during a treatment session.

While the air distribution system 1000 has been described as including a pump 1004 for generating and supplying positive and negative pressure, other types of pressure generating devices can alternatively or additionally be used. One example of another suitable device is the Hargraves BTC-IIS, single body, dual head Miniature Diaphragm Pump and Compressor.

While a system vacuum is described as application of a vacuum using each of the vacuum ports 151, the annular passages 137A, 137B, and the annular passages 147A, 147B, in some embodiments, the system vacuum may be applied through only a subset of these ports.

In some implementations, the cassette 112 is fluidly coupled to one or more solution bags (e.g., dialysate bags 122 and heater bag 124 of FIG. 1) through one or more solution lines (e.g., dialysate bag lines 126 and heater bag line 128 of FIG. 1) prior to testing the cassette 112 for leaks, and valves along the solution lines fluidly coupling the cassette 112 to the solution bags are closed prior to leak testing in order to prevent fluid flow along the solution lines.

While the air distribution system 1000 uses pressurized air and vacuum to actuate the inflatable members 142 and the inflatable pad 135 and to draw the membrane 140 against the piston heads 134A, 134B and other surfaces of the cassette interface 110, gases other than air can alternatively or additionally be supplied throughout the air distribution system. Also, the inflatable members 142 and inflatable pad 135 can be replaced with mechanically actuated devices. Similarly, the pistons can be replaced with hydraulic or pneumatic devices such as diaphragm pumps.

While the vacuum and pressure sensors of the air distribution system 1000 have been described as being connected to air lines leading to the vacuum reservoir, other arrangements are possible. In certain implementations, for example, the vacuum and pressure sensors are all part of an input/output board of the PD cycler 102.

While the piston heads 134A, 134B of the PD cyclers above have been described as being hemispherical, the piston heads could be any of various other shapes. In some implementations, for example, the piston heads can have flat end surfaces. In such implementations, the cup-shaped members disposed in the pump chambers of the cassette can have flat surfaces that abut the flat end surfaces of the piston heads during use. Similarly, while the piston heads 134A, 134B have been described as being formed using certain materials and manufacturing techniques, any of various other suitable materials and manufacturing techniques could alternatively be used.

While the inflatable pad 135 and the inflatable members 142 have been described as being pressurized and inflated using an air pump 1004, in some implementations the inflatable pad 135 and the inflatable members 142 are pressurized and inflated using a positive pressure tank. For example, in some implementations, a positive pressure tank containing air that is positively pressurized is connected to the manifold 1012 of the air distribution system 1000. The air within the positive pressure tank can, for example, be pressurized to a pressure of about 20 psi to about 60 psi (e.g., about 40 psi). During use, the manifold 1012 can be operated in a manner such that pressurized air is supplied from the positive pressure tank to the inflatable members 142 and/or to the inflatable pad 135. For example, by opening valves of a manifold associated with an air line coupled to the positive pressure tank, positive pressure can be supplied from the positive pressure tank to the inflatable members 142 and/or to the inflatable pad 135 in the door 108 of the PD cycler 102. The positive pressure tank can be used instead of or in addition to the air pump 1004 for delivering positive pressure to the inflatable pad 135 and the inflatable members 142. By limiting operation of the air pump 1004, the noise level associated with operating the PD cycler 102 can advantageously be reduced.

While the cassettes discussed above have been described as having two pump chambers, the cassettes can alternatively have more or fewer than two pump chambers.

While certain PD cyclers above have been described as including a touch screen and associated buttons, the PD cycler can include other types of screens and user data entry systems. In certain implementations, for example, the cycler includes a display screen with buttons (e.g., feathertouch buttons) arranged on the console adjacent the display screen. Certain buttons can be arranged to be aligned with operational options displayed on the screen during use such that the user can select a desired operational option by pressing the button aligned with that operational option. Additional buttons in the form of arrow buttons can also be provided to allow the user to navigate through the various display screens and/or the various items displayed on a particular screen. Other buttons can be in the form of a numerical keypad to allow the user to input numerical values in order, for example, to input operational parameters. A select or enter button can also be provided to allow the user to select an operational option to which the user navigated by using the arrow keys and/or to allow the user to enter values that the user inputted using the numerical keypad.

While the doors of the PD cyclers described above are shown as being positioned on a front face of the PD cyclers, the doors can alternatively be positioned at various other locations on the PD cyclers. For example, the doors could be positioned on a top face of the PD cycler such that the cassette is slid into the cassette compartment in a substantially horizontal orientation instead of a substantially vertical orientation.

While some of the PD cyclers discussed above have been described as including inflatable pads in their doors to compress the cassette between the door and the cassette interface, the PD cyclers can alternatively or additionally include inflatable pads positioned behind the cassette interface.

While the cassettes described above have been described as being part of a PD system, these types of cassettes can be used in any of various other types of cassette-based medical fluid pumping systems. Other examples of medical fluid pumping systems with which cassettes described herein can be used include hemodialysis systems, blood perfusion systems, and intravenous infusion systems.

While the cassettes have been described as being used to pump dialysate, other types of dialysis fluids can be pumped through the cassettes. As an example, in the case of cassettes used with hemodialysis machines, blood can be pumped through the cassettes. In addition, priming solutions, such as saline, can similarly be pumped through cassettes using the various different systems and techniques described above. Similarly, as an alternative to dialysis fluids, any of various other types of medical fluids can be pumped through the above-described cassettes depending on the type of medical fluid pumping machines with which the cassettes are used.

A selected illustrative embodiment is described above in some detail. It should be understood that only structures considered necessary for clarifying the present disclosure have been described herein. Other conventional structures, and those of ancillary and auxiliary components of the system, are assumed to be known and understood by those skilled in the art. Moreover, while a working example has been described above, the present disclosure is not limited to the working example described above, but various design alterations may be carried out without departing from the present disclosure as set forth in the claims.

What is claimed is:

1. A method of detecting micro-leaks in a medical fluid cassette, the method comprising:
   decreasing a pressure between a vacuum reservoir of a medical treatment machine and a membrane of the medical fluid cassette to a decreased predetermined pressure when the medical fluid cassette is coupled to the medical treatment machine;
   measuring, using a flow meter, a rate of net fluid flow between the vacuum reservoir and the membrane of the medical fluid cassette while maintaining the decreased predetermined pressure;
   determining that the rate of net fluid flow between the vacuum reservoir and the membrane of the medical fluid cassette is above a threshold value; and
   in response to determining that the rate of net fluid flow is above the threshold value, causing the medical treatment machine to take a particular action.

2. The method of claim 1, wherein causing the medical treatment machine to take a particular action comprises causing the medical treatment machine to generate at least one of an audible indication, a visual indication, and a tactile indication.

3. The method of claim 2, wherein the at least one of an audible indication, a visual indication, and a tactile indication indicates to a user that the membrane of the medical fluid cassette has a micro-leak.

4. The method of claim 3, wherein the at least one of an audible indication, a visual indication, and a tactile indication comprises a message displayed on a screen of the medical treatment machine.

5. The method of claim 3, wherein the at least one of an audible indication, a visual indication, and a tactile indication comprises an audible warning emitted by a speaker of the medical treatment machine.

6. The method of claim 1, wherein causing the medical treatment machine to take a particular action comprises terminating a treatment being carried out by the medical treatment machine.

7. The method of claim 1, wherein causing the medical treatment machine to take a particular action comprises disabling the medical treatment machine until the medical fluid cassette is replaced with a new medical fluid cassette that does not contain a leak.

8. The method of claim 1, wherein
the flow meter comprises a micro-flow meter; and
measuring the rate of net fluid flow between the membrane of the medical fluid cassette and the vacuum reservoir of the medical treatment machine comprises monitoring, using the micro-flow meter, the rate of net fluid flow between the membrane and the vacuum reservoir of the medical treatment machine during application of a vacuum pressure on membrane of the medical fluid cassette during a testing period.

9. The method of claim 8, wherein:
the medical treatment machine is a dialysis machine; and
the medical fluid cassette is a dialysis fluid cassette.

10. The method of claim 9, wherein the medical treatment machine is configured to perform a peritoneal dialysis treatment.

11. The method of claim 8, wherein the medical fluid cassette is a medical fluid pumping cassette.

12. The method of claim 11, wherein the medical fluid pumping cassette is a dialysate pumping cassette.

13. The method of claim 1, wherein the threshold value is between 1.25 cc/min and 1.75 cc/min.

14. The method of claim 1, wherein determining that the rate of net fluid flow is above the threshold value indicates that the membrane of the medical fluid cassette has an opening through the membrane no greater than 0.005 inches in diameter.

15. The method of claim 1, further comprising:
determining that the rate of net fluid flow is above an upper boundary; and
in response to determining that the rate of net fluid flow is above an upper boundary, identifying the medical fluid cassette as having a leak greater than a micro-leak.

16. A medical treatment system comprising:
a medical fluid cassette comprising a body and a membrane affixed to the body;
a medical fluid treatment machine comprising
a vacuum reservoir;
a flow meter positioned between the vacuum reservoir and the membrane of the medical fluid cassette when the medical fluid cassette is coupled to the medical fluid treatment machine; and
at least one processor configured to perform operations comprising:
controlling the medical fluid treatment machine to decrease a pressure between the vacuum reservoir and the membrane of the medical fluid cassette to a decreased predetermined pressure;
receiving, from the flow meter, data indicating a rate of net fluid flow between the vacuum reservoir and the membrane of the medical fluid cassette while maintaining the decreased predetermined pressure;
determining, based on the data received from the flow meter, that the rate of net fluid flow between the vacuum reservoir and the membrane of the medical fluid cassette is above a threshold value; and in response to determining that the rate of net fluid flow is above the threshold value, causing the medical fluid treatment machine to take a particular action.

17. The medical treatment system of claim 16, wherein causing the medical fluid treatment machine to take a particular action comprises causing the medical fluid treatment machine to generate at least one of an audible indication, a visual indication, and a tactile indication.

18. The medical treatment system of claim 17, wherein the at least one of an audible indication, a visual indication, and a tactile indication indicates to a user that the membrane of the medical fluid cassette has a micro-leak.

19. The medical treatment system of claim 18, wherein the at least one of an audible indication, a visual indication, and a tactile indication comprises a message displayed on a screen of the medical fluid treatment machine.

20. The medical treatment system of claim 18, wherein the at least one of an audible indication, a visual indication, and a tactile indication comprises an audible warning emitted by a speaker of the medical fluid treatment machine.

21. The medical treatment system of claim 16, wherein causing the medical fluid treatment machine to take a particular action comprises terminating a treatment being carried out by the medical fluid treatment machine.

22. The medical treatment system of claim 16, wherein causing the medical fluid treatment machine to take a particular action comprises disabling the medical fluid treatment machine until the medical fluid cassette is replaced with a new medical fluid cassette that does not contain a leak.

23. The medical treatment system of claim 16, wherein the medical fluid treatment machine is a dialysis machine.

24. The medical treatment system of claim 16, wherein:
the medical fluid treatment machine comprises a vacuum line fluidly coupling the vacuum reservoir and the membrane of the medical fluid cassette; and
the flow meter comprises a micro-flow meter positioned along the vacuum line.

25. The medical treatment system of claim 16, wherein the data indicating the rate of net fluid flow between the vacuum reservoir and the membrane of the medical fluid cassette comprises fluid flow measurements captured by the flow meter during a particular testing period.

26. The medical treatment system of claim 16, wherein the threshold value is between 1.25 cc/min and 1.75 cc/min.

27. The medical treatment system of claim 16, wherein detecting that the rate of net fluid flow is above the threshold value indicates that the membrane of the medical fluid cassette has an opening through the membrane no greater than 0.005 inches in diameter.

28. The medical treatment system of claim 16, wherein the medical fluid treatment machine comprises a surface that abuts the medical fluid cassette when the medical fluid cassette is coupled to the medical fluid treatment machine, and the surface defines one or more vacuum ports.

29. The medical treatment system of claim 16, wherein:
the medical fluid treatment machine includes a pump fluidly coupled to the vacuum reservoir; and
controlling the medical fluid treatment machine to decrease a pressure between the vacuum reservoir and the membrane of the medical fluid cassette comprises operating the pump.

* * * * *